United States Patent
Davison et al.

(10) Patent No.: US 6,911,476 B2
(45) Date of Patent: Jun. 28, 2005

(54) SULFONAMIDE DERIVATIVES

(75) Inventors: Joshua Zwick Davison, Indianapolis, IN (US); Winton Dennis Jones, Carmel, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 7 days.

(21) Appl. No.: 10/204,339

(22) PCT Filed: Feb. 26, 2001

(86) PCT No.: PCT/US01/04929
§ 371 (c)(1),
(2), (4) Date: Aug. 15, 2002

(87) PCT Pub. No.: WO01/068592
PCT Pub. Date: Sep. 20, 2002

(65) Prior Publication Data
US 2003/0225266 A1 Dec. 4, 2003

Related U.S. Application Data

(60) Provisional application No. 60/234,651, filed on Sep. 22, 2000, and provisional application No. 60/188,806, filed on Mar. 13, 2000.

(51) Int. Cl.[7] ............... C07C 311/04; C07C 311/08; C07D 317/54; A61K 31/18; A61P 25/00
(52) U.S. Cl. ............... 514/604; 514/605; 564/97; 564/99; 564/92
(58) Field of Search ............... 564/92, 97, 99; 514/604, 605

(56) References Cited

U.S. PATENT DOCUMENTS

| | | | |
|---|---|---|---|
| 2,592,364 A | 4/1952 | Weissberger et al. | |
| 3,535,328 A | 10/1970 | Zielinski | |
| 4,152,112 A | 5/1979 | Bugaut et al. | |
| 4,929,530 A | 5/1990 | Saeki et al. | |
| 6,262,096 B1 * | 7/2001 | Kim et al. | 514/369 |
| 6,596,719 B1 * | 7/2003 | Bolli et al. | 514/235.8 |

FOREIGN PATENT DOCUMENTS

| | | |
|---|---|---|
| DE | 120047 | 2/2000 |
| EP | 0 471 236 | 2/1992 |
| GB | 2065121 | 6/1981 |
| WO | WO 98/33496 | 2/1997 |
| WO | WO-9828264 A1 * | 7/1998 |
| WO | WO-9915129 A2 * | 4/1999 |
| WO | WO-9916453 A1 * | 4/1999 |
| WO | WO 00/06537 | 2/2000 |
| WO | WO-0116103 A1 * | 3/2001 |

OTHER PUBLICATIONS

Tzschentke TM. Amino Acids 23(1–3): 147–152, 2002.*
Palucha et al., Pol. J. Pharmacol. 54(6): 581–586, 2002.*
Martinez–Turrillas et al., 43(8): 1230–1237, 2002.*
Patent Abstracts of Japan, vol. 015, No. 133 (C–0820), Apr. 2, 1991 and JP 03 017053A (Fuji Photo Film), Jan. 25, 1991 abstract.
H. H. Eckenroth, et al.: "Uber einige Derivate des o–Benzoesauresulfinids (Saccharin) II". Berichte Der Deutschen Chemischen Gesellschaft, vol. 30, 1897, pp. 1265–1269, XP002174085, Verlag Chemie, Weinheim, DE, p. 1268.
Chemical Abstracts, vol. 94, No. 19, May 11, 1981, abstract No. 155973J, V.I. Markov, et al: 1–Arenesulphonyl–2, 2–dimethylaziridines, p. 578; XP002174090 abstract and Chemical Abstracts 10th Collective Chemical Substances Index, p. 7573CS XP002174086– American Chemical Society, Washington, DC, US ISSN: 0009–2258 & Ukrainskii Khimicheskii Zhurnal, vol. 47, No. 1, 1981, pp. 80–84, National Academy of Sciences of the Urkaine, Kiev, UA, ISSN: 0041–6045, CAS RN 77225–83–3, N–(2–methyl–2–phenoxypropyl)benzenesulphonamide.
H. Togo, et al.: Study on radical amidation onto aromatic rings with (diacyloxyiodo)arenas, Journal of Organic Chemistry, vol. 63, No. 15, Mar. 7, 1998, pp. 5193–5200, XP–002174087.
R.A. Bartsch, et al.: A novel 12–membered triazaoxamacrocycle–N,N',N"–triacetic acid Indicator for colorimetric determination of calcium, Journal of Organic Chemistry, vol. 58, No. 17, Aug. 13, 1993, pp. 4681–4684, XP002174088.
J.S. Bradshaw, et al.: Facile synthesis of benzene–bridged azaoxamacrocyclic ligands, Journal of Heterocyclic Chemistry, vol. 35, No. 3, May 1998, pp. 519–524, XP002174089.
E. Sartory, et al.: Synthesis and activities of new arylsulphonamido thromboxane A2 receptor antagonists, European Journal of Medicinal Chemistry, vol. 28, No. 7–8, 1993, pp. 625–632, XP000396678.

* cited by examiner

*Primary Examiner*—Venkataraman Balasubramanian
(74) *Attorney, Agent, or Firm*—John A. Cleveland, Jr.; Nelsen L. Lentz

(57) ABSTRACT

The present invention provides certain sulfonamide derivatives useful for potentiating glutamate receptor function in a patient and therefore, useful for treating a wide variety of conditions, such as psychiatric and neurological disorders.

17 Claims, No Drawings

SULFONAMIDE DERIVATIVES

This is a 371 of PCT/US01/04929 filed Feb. 26, 2001 which claims priority to U.S. Provisional Application No. 60/188,806 filed Mar. 13, 2000 and provisional application No. 60/234,651 filed Sep. 22, 2000.

BACKGROUND OF THE INVENTION

The present invention relates to the potentiation of glutamate receptor function using certain sulfonamide derivatives. It also relates to novel sulfonamide derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are not fully understood.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron.* Vol. 11, 1069–1082, 1993.

International Patent Application Publication Number WO 9625926 discloses a group of phenylthioalkylsulfonamides, S-oxides and homologs which are said to potentiate membrane currents induced by kainic acid and AMPA.

U.S. Pat. No. 3,143,549 discloses certain phenylalkylsulfamides, including 1-methyl-2-phenylethyl dimethylsulfamide. The compounds are said to have central nervous system activity, in particular anti-anxiety and tranquilizing properties.

U.S. Pat. No. 3,267,139 discloses certain N'-trimethylacetyl-N-phenylalkysulfamides and -phenylcyclopropylsulfamides having central nervous system activity and anticonvulsant activity. The compounds are also said to produce Parkinson-like symptoms in experimental animals.

U.S. Pat. No. 3,860,723 discloses a method of increasing feed intake of healthy animals using certain phenylalkylsulfamides.

Foye et al., *J. Pharm. Sci.* (1971), 60(7), 1095–6 discloses certain phenylalkyl methylsulfonamides including N-1-methyl-2-phenylethyl methanesulfonamide, having hypotensive activity.

British Patent Specification Number 1,059,360 discloses certain phenylalkylsulfamides having activity as sedatives, narcotics and anti-convulsants, including 1-(1-methyl-2-phenylethylaminosulphonyl)piperidine.

U.S. Pat. No. 4,210,749 discloses N-1-methyl-2-phenyl-3-methoxy ethyl butane-sulfonamide.

Gualtieri et al., *J. Pharm. Sci.*, (1973), 62(5), 849–851 discloses N-1-methyl-2-phenylethyl butanesulfonamide and its evaluation as a mosquito repellent.

Foye et al., *J. Pharm. Sci.* (1979), 68(5), 591–5 discloses N-1-methyl-2-(4-chlorophenyl)ethyl methane-sulfonamide.

Foye and Sane, *J. Pharm. Sci.* (1977), 66(7), 923–6 discloses N-methanesulfonyl and N-trifluoromethanesulfonyl derivatives of amphetamines and certain 4-substituted analogs thereof, and their evaluation for central nervous system and anorexic effects.

European patent application publication no. EP-A1-0657442 discloses certain naphthyloxyacetic acid derivatives as PEG2 agonists and antagonists. N-(2,2-dephenylethyl)-methanesulfonamide is disclosed as an intermediate at page 53, line 38.

U.S. Pat. No. 3,629,332 discloses certain N-aryl- and N-heteroarylalkyl fluoroalkane sulfonamides as plant growth modifiers, including N-(alpha-methylphenylethyl) trifluoromethanesulfonamide, difluoromethanesulfonamide and fluoromethanesulfonamide. Some of the compounds are also said to have other biological activity, including insecticidal, acaricidal, nematicidal, analgesic and anti-inflammatory activity.

AMPA receptor potentiators have been shown to improve memory in a variety of animal tests. Staubli et al., *Proc. Natl. Acad. Sci.*, Vol. 91, pp 777–781, 1994, *Neurobiology*, and Arai et al., *The Journal of Pharmacology and Experimental Therapeutics*, 278: 627–638, 1996.

In addition, certain sulfonamide derivatives which potentiate glutamate receptor function in a mammal have been disclosed in the following International Patent Application Publications: WO 98/33496 published Aug. 6, 1998; WO 99/43285 published Sep. 2, 1999; WO 00/06539; WO 00/06537, WO 00/06176, WO 00/06159, WO 00/06158, WO 00/06157, WO 00/06156, WO 00/06149, WO 00/06148, and WO 00/06083, all published Feb. 10, 2000; and WO 00/66546 published Nov. 9, 2000.

The present invention provides compounds of formula I:

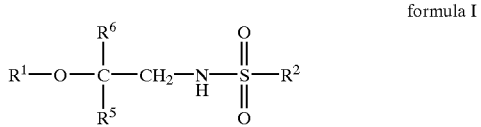

formula I wherein
$R^1$ represents an unsubstituted or substituted aromatic group, or an unsubstituted or substituted heteroaromatic group;
$R^2$ represents (1–6C)alkyl, (3–6C)cycloalkyl, fluoro(1–6C)alkyl, chloro(1–6C)alkyl, (2–6C)alkenyl, phenyl which is unsubstituted or substituted by halogen, (1–4C)alkyl or (1–4C)alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group;
$R^5$ represents hydrogen, (1–6C)alkyl; (2–6C)alkenyl; or aryl; and
$R^6$ represents hydrogen, (1–6C)alkyl; (2–6C)alkenyl; or aryl;
or a pharmaceutically acceptable salt thereof.

The present invention further provides a method of potentiating glutamate receptor function in a patient, which comprises administering to said patient an effective amount of a compound of formula I.

The present invention provides a method of treating cognitive disorders in a patient, which comprises administering to said patient an effective amount of a compound of formula I.

The present invention provides a method of treating depression in a patient, which comprises administering to said patient an effective amount of a compound of formula I.

The present invention provides a method of treating Alzheimer's disease in a patient, which comprises administering to said patient an effective amount of a compound of formula I.

In addition, the present invention further provides a method of treating psychosis or cognitive deficits associated with psychosis in a patient, which comprises administering to said patient an effective amount of a compound of formula I.

According to another aspect, the present invention provides the use of a compound of formula I, or a pharmaceutically acceptable salt thereof for the manufacture of a medicament for potentiating glutamate receptor function.

In addition, the present invention provides the use of a compound of formula I or a pharmaceutically acceptable salt thereof for potentiating glutamate receptor function.

The invention further provides pharmaceutical compositions comprising, a compound of formula I and a pharmaceutically acceptable diluent or carrier.

This invention also encompasses novel intermediates, and processes for the synthesis of the compounds of formula I.

DETAILED DESCRIPTION OF THE INVENTION

In this specification, the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Hungtington's chorea, myoclonus and Parkinson's disease; reversal of drug-induced states (such as cocaine, amphetamines, alcohol-induced states); depression; attention deficit disorder; attention deficit hyperactivity disorder; psychosis; cognitive deficits associated with psychosis, drug-induced psychosis, and sexual dysfunction. The compounds of formula I may also be useful for improving memory (both short term and long term) and learning ability. The present invention provides the use of compounds of formula I for the treatment of each of these conditions.

The present invention includes the pharmaceutically acceptable salts of the compounds defined by formula I. A compound of this invention can possess a sufficiently acidic group, a sufficiently basic group, or both functional groups, and accordingly react with any of a number of organic and inorganic bases, and inorganic and organic acids, to form a pharmaceutically acceptable salt. The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. Such salts include the pharmaceutically acceptable salts listed in *Journal of Pharmaceutical Science*, 66, 2–19 (1977), which are known to the skilled artisan. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, 1-naphthalenesulfonate, 2-napththalenesulfonate, 1,5-naphthalenedisulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as aryl, and includes phenyl and a polycyclic aromatic carbocyclic ring such as 1- or 2-naphthyl, 1,2-dihydronaphthyl, 1,2,3,4-tetrahydronaphthyl, and the like.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl, and quinolyl.

The term "substituted" as used in the term "substituted aromatic or heteroaromatic group" herein signifies that one or more (for example one or two) substituents may be present, said substituents being selected from atoms and groups which, when present in the compound of formula I, do not prevent the compound of formula I from functioning as a potentiator of glutamate receptor function.

Examples of substituents which may be present in a substituted aromatic or heteroaromatic group group include halogen; nitro; cyano; hydroxyimino; (1–10C) alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C) alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl (1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C)alkoxycarbonyl dimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$-$(L^a)_n$-$X^2$-$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, $OCONR^{19}$, N(CO(1–4C)alkyl)CO, or $NR^{19}COO$, $R^{15}$ represents hydrogen, (1–10C)alkyl, phenyl(1–4C)alkyl, halo (1–10C)alkyl, (1–4C)alkoxycarbonyl(1–4C)alkyl, (1–4C)alkylsulfonylamino(1–4C)alkyl, (1–4C)alkylaminosulfonyl (1–4C)alkyl, N-(1–4C)alkoxycarbonyl)(1–4C)alkylsulfonylamino(1–4C)alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

The term (1–10C)alkyl includes (1–8C)alkyl, (1–6C)alkyl and (1–4C)alkyl. Particular values are methyl, ethyl, propyl, isopropyl, butyl, isobutyl, t-butyl, pentyl, hexyl, heptyl, octyl, nonyl and decyl.

The term (2–10C)alkenyl includes (3–10C)alkenyl, (2–8C)alkenyl, (2–6C)alkenyl and (2–4C)alkenyl. Particular values are vinyl and prop-2-enyl.

The term (2–10C)alkynyl includes (3–10C)alkynyl, (2–8C)alkynyl, (2–6C)alkynyl and (3–4C)alkynyl. A particular value is prop-2-ynyl.

The term (3–8C)cycloalkyl, as such or in the term (3–8C)cycloalkyloxy, includes monocyclic and polycyclic groups. Particular values are cyclopropyl, cyclobutyl, cyclopentyl, cyclohexyl and bicyclo[2.2.2]octane. The term includes (3–6C)cycloalkyl: cyclopropyl, cyclobutyl, cyclopentyl and cyclohexyl.

As used herein the terms "integer of from 1 to 4" or "integer of from 1 to 3" includes the integers 1, 2, 3, and 4, or the integers 1, 2, and 3, respectively.

The term (5–8C)cycloalkyl includes cyclopentyl, cyclohexyl, cycloheptyl and cyclooctyl.

The term hydroxy(3–8C)cycloalkyl includes hydroxycyclopentyl, such as 3-hydroxycyclopentyl.

The term oxo(3–8C)cycloalkyl includes oxocyclopentyl, such as 3-oxocyclopentyl.

The terms "halogen", "Hal" or "halide" include fluorine, chlorine, bromine and iodine unless otherwise specified.

The term halo(1–10C)alkyl includes halo(1–6C)alkyl, halo(1–4C)alkyl, fluoro(1–10C)alkyl, fluoro(1–6C)alkyl, fluoro(1–4C)alkyl, chloro(1–6C)alkyl and chloro(1–4C)alkyl, such as trifluoromethyl, 2,2,2-trifluoroethyl, and chloromethyl.

The term (1–10C)alkoxy includes (1–6C)alkoxy and (1–4C)alkoxy, such as methoxy, ethoxy, propoxy, isopropoxy and isobutoxy.

The term cyano(2–10C)alkenyl includes 2-cyanoethenyl.

The term (2–4C)alkylene includes ethylene, propylene and butylene. A preferred value is ethylene.

The term thienyl includes thien-2-yl and thien-3-yl.

The term furyl includes fur-2-yl and fur-3-yl.

The term oxazolyl includes oxazol-2-yl, oxazol-4-yl and oxazol-5-yl.

The term isoxazolyl includes isoxazol-3-yl, isoxazol-4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol-4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol-4-yl and isothiazol-5-yl.

The term imidazolyl includes imidazol-2-yl, imidazolyl-4-yl and imidazolyl-5-yl.

The term triazolyl includes [1,2,4]triazol-3-yl and [1,2,4]triazol-5-yl.

The term tetrazolyl includes tetrazol-5-yl.

The term pyridyl includes pyrid-2-yl, pyrid-3-yl and pyrid-4-yl.

The term pyridazinyl includes pyridazin-3-yl, pyridazin-4-yl, pyridazin-5-yl and pyridazin-6-yl.

The term pyrimidyl includes pyrimidin-2-yl, pyrimidin-4-yl, pyrimidin-5-yl and pyrimidin-6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.

The term benzoxazolyl includes benzoxazol-2-yl.

The term benzothiazolyl includes benzothiazol-2-yl.

The term indolyl includes indol-2-yl and indol-3-yl.

The term quinolyl includes quinol-2-yl.

The term dihydrothiazolyl includes 4,5-dihydrothiazol-2-yl, and the term (1–4C)alkoxycarbonyldihydrothiazolyl includes 4-methoxycarbonyl-4,5-dihydrothiazol-2-yl.

The term -(1–4C)alkyl(3–8C)cycloalkyl includes the following:

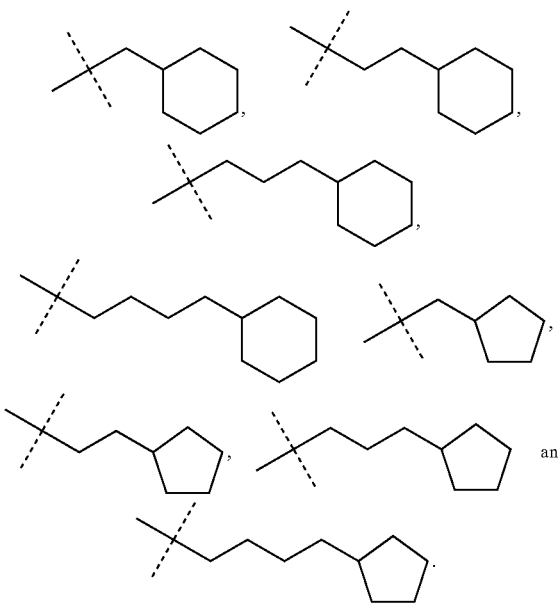

The term -(1–4C)alkylaromatic includes the following:

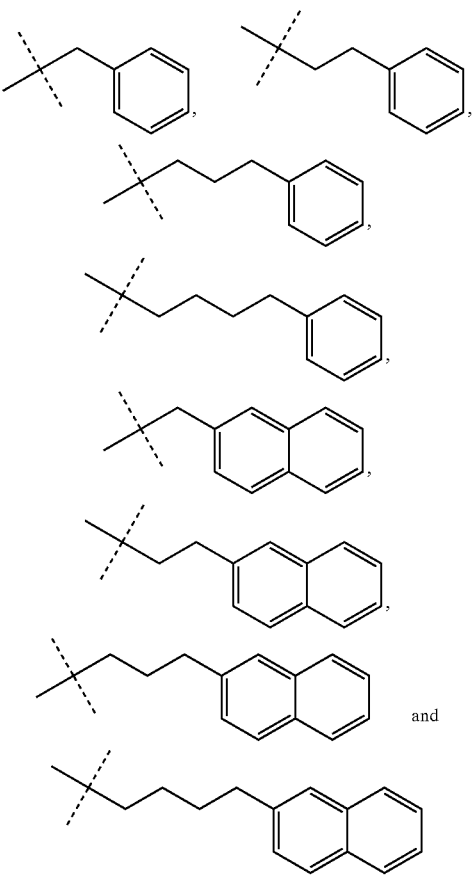

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2-enyl, methoxyethyl, phenyl, 4-fluorophenyl, or dimethylamino. Preferably $R^2$ is ethyl, 2-propyl or dimethylamino.

Examples of values for $R^9$ are hydrogen, methyl, ethyl, propyl, isopropyl, t-butyl, ethenyl, cyclopropyl, cyclobutyl, cyclopentyl, cyclohexyl, 2-pyrrolidinyl, morpholino or 2-tetrahydrofuryl.

$R^9$ is preferably (1–4C)alkyl, (2–4C)alkenyl, (3–6C)cycloalkyl, pyrrolidinyl, morpholino or tetrahydrofuryl.

Examples of values for $R^{15}$ are hydrogen, methyl, ethyl, propyl, isopropyl, butyl, t-butyl, benzyl, 2,2,2-trifluoroethyl, 2-methoxycarbonylethyl, cyclohexyl, 10-camphoryl, phenyl, 2-fluorophenyl, 3-fluorophenyl, 2-trifluoromethylphenyl, 4-trifluoromethylphenyl, 2-methoxyphenyl, 3-methoxyphenyl, 4-methoxyphenyl, 1-(5-dimethylamino)naphthyl, and 2-thienyl.

$X^1$ preferably, represents O, CO, CONH or NHCO.

z is preferably 0.

Particular values for the groups $(CH_2)_y X^1 R^9$ and $(CH_2)_z X^3 R^{15}$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C)alkenyloxy, such as prop-2-enyloxy; (3–10C)alkynyloxy, including (3–6C)alkynyloxy, such as prop-2-ynyloxy; and (1–6C)alkanoyl, such as formyl and ethanoyl.

Examples of particular values for y are 0 and 1.

Examples of particular values for z are 0, 1, 2 and 3.

$L^a$ and $L^b$ preferably each independently represents $CH_2$.

$X^2$ preferably represents a bond, O, NH, CO, CH(OH), CONH, NHCONH or $OCH_2CONH$, with a bond, O, and CONH being especially preferred.

Preferably the group $(CH_2)_y X^1 R^9$ represents CHO; $COCH_3$, $OCH_3$; $OCH(CH_3)_2$; $NHCOR^9$ in which $R^9$ represents methyl, ethyl, isopropyl, t-butyl, ethenyl, cyclopropyl, cyclobutyl, cyclopentyl, cyclohexyl, 2-pyrolidinyl or morpholino; $CONHR^9$ in which $R^9$ represents cyclopropyl or cyclopentyl; NHCOCOOCH3; or 2-tetrahydrofurylmethoxy.

Preferably the group $(CH_2)_z X^3 R^{15}$ represents $NH_2$; $CH_2NH_2$; $(CH_2)_2NH_2$; $(CH_2)_3NH_2$; $CONH_2$; $CONHCH_3$; $CON(CH_3)_2$; $N(C_2H_5)_2$; $CH_2OH$; $CH(OH)CH_3$; $CH(OH)CH_2CH_2$; CHO; $COCH_3$; COOH; $COOCH_3$; $CH_2NHCOOC(CH_3)_3$; $(CH_2)_2NHCOOC(CH_3)_3$; $SO_2NH_2$; $NHSO_2CH_3$; $NHSO_2CH(CH_3)_2$, $OCH(CH_3)CH_2NHSO_2CH(CH_3)_2$, $N(COCH_3)_2$; a group of formula $(CH_2)_2NHSO_2R^{15}$ in which $R^{15}$ represents $CH_3$, $CH_2CH_3$, $CH(CH_3)_2$, $(CH_2)_2CH_3$, $(CH_3)_3CH_3$, benzyl, $CH_2CF_3$, 2-methoxycarbonylethyl, cyclohexyl, 10-camphoryl, phenyl, 2-fluorophenyl, 4-fluorophenyl, 2-trifluoromethylphenyl, 4-trifluoromethylphenyl, 4-methoxyphenyl, 1-(2-dimethylamino)naphthyl or 2-thienyl; CH(OH) $CH_2NHSO_2CH_3$; $(CH_2)_3NHSO_2CH(CH_3)_2$; $COCH_2N(OCOC(CH_3)_2SO_2CH_3$; $COCH_2NHSO_2CH_3$; $(CH_2)_2 NHCOR^{15}$ in which $R^{15}$ represents $CH_3$, $CH(CH_3)_2$, $CH_2CH(CH_3)_2$, phenyl, 3-fluorophenyl, 4-fluorophenyl, benzyl, 2-methoxyphenyl, 4-methoxyphenyl, 2-thienyl, CH=CH, CH=CHCN, $OCH_3$ or $O(CH_2)_3CH_3$.

Examples of particular values for $(L^a)_n$-$X^2$-$(L^b)_m$ are a bond, O, NH, S, SO, $SO_2$, CO, $CH_2$, $COCH_2$, COCONH, $CH(OH)CH_2$, CONH, NHCO, NHCONH, $CH_2O$, $OCH_2$, $OCH_2CONH$, $CH_2NH$, $NHCH_2$ and $CH_2CH_2$, with a bond, CONH, and $CH_2O$ being especially preferred.

$R^{14}$ is preferably an unsubstituted or substituted phenyl, naphthyl, furyl, thienyl, isoxazolyl, thiazolyl, tetrazolyl, pyridyl, pyrimidyl benzothienyl or benzothiazolyl group.

Examples of particular values for $R^{14}$ are phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-difluoro-phenyl, 2,4-difluorophenyl, 3,5-difluorophenyl, 3,4-dichlorophenyl, 3,5-dichlorophenyl, 4-cyanophenyl, 3-nitrophenyl, 4-hydroxyiminophenyl, 2-methylphenyl, 4-methylphenyl, 4-ethylphenyl, 3-propylphenyl, 4-t-butylphenyl, 2-prop-2-enylphenyl, 4-(4-(1,1-dioxotetrahydro-1,2-thiazinyl)phenyl, 2-trifluoromethylphenyl, 3-trifluoromethylphenyl, 4-trifluoromethylphenyl, 2-bromomethylphenyl, 2-fluoro-4-trifluoromethylphenyl, 4-(2-cyanoethenyl)phenyl, 4-phenyl, 2-formylphenyl, 3-formylphenyl, 4-formylphenyl, 2-acetylphenyl, 3-acetylphenyl, 4-acetylphenyl, 2-propanoylphenyl, 2-(2-methyl-propanoyl)phenyl, 2-methoxyphenyl, 3-methoxyphenyl, 4-methoxyphenyl, 4-butoxyphenyl, 2-hydroxymethylphenyl, 4-hydroxymethylphenyl, 2-(1-hydroxyethyl)phenyl, 3-(1-hydroxyethyl)phenyl, 4-(1-hydroxyethyl)phenyl, 2-(1-hydroxypropyl)phenyl, 4-(1-hydroxypropyl)phenyl, 2-(1-hydroxy-2,2-dimethyl-propyl)phenyl, 4-trifluoromethoxyphenyl, 2-aminophenyl, 4-aminophenyl, 4-N,N-diethylaminophenyl, 4-aminomethylphenyl, 4-(2-aminoethyl)phenyl, 4-(3-aminopropyl)phenyl, 4-carboxyphenyl, 4-carbamoylphenyl, 4-N-methylcarbamoylphenyl, 4-N,N-dimethylcarbamoylphenyl, 2-isopropylaminomethylphenyl, 4-t-butoxycarbonylaminomethylphenyl, 4-(2-isopropoxy-carboxamido)ethylphenyl, 4-(2-t-butoxycarboxamido)ethyl-phenyl, 4-isopropylsulfonylaminophenyl, 4-(2-methane-sulfonylamino)ethylphenyl, 4-(2-ethylsulfonylamino)ethyl-phenyl, 4-(3-isopropylsulfonylamino)propylphenyl, 4-(1-(2-(2-propane)sulfonylamino)propyl)phenyl, 4-(2-propylsulfonyl-amino)ethylphenyl, 4-(2-isopropylsulfonylamino)ethylphenyl, 4-(2-butylsulfonylamino)ethylphenyl, 4-(1-isopropyl-sulfonylaminomethyl)ethylphenyl, 4-(1-hydroxy-2-methane-sulfonylamino)ethylphenyl, 4-(2-(2,2,2-trifluoroethyl)-sulfonylaminoethyl)phenyl, 4-(2-cyclohexylsulfonylamino)-ethylphenyl, 4-(2-(2,2,2-trifluoroethyl)sulfonylamino)-ethylphenyl, 4-(2-N,N-dimethylaminosulfonylamino)-ethylphenyl, 4-(2-phenylsulfonylaminoethyl)phenyl, 4-(2-(2-fluorophenyl) sulfonylaminoethyl)phenyl, 4-(2-(4-fluoro-phenyl) sulfonylaminoethyl)phenyl, 4-(2-(2-trifluoromethyl-phenyl) sulfonylaminoethyl)phenyl, 4-(2-(4-trifluoro-methylphenyl) sulfonylaminoethyl)phenyl, 4-(2-(4-methoxyphenyl) sulfonylaminoethyl)phenyl, 4-(2-(1-(5-dimethylamino) napthalenesulfonylamino)ethyl)phenyl, 4-(2-(2-thienyl) sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(1-(2-(2-methoxy-carbonylethanesulfonylamino)ethyl)phenyl, 4-(1-(2-(10-camphorsulfonylamino)ethyl)phenyl, 4-(1-(2-(benzylsulfonyl-amino)ethyl)phenyl, 4-(2-phenylacetamido)ethyl)phenyl, 4-methanesulfonylaminoethanoylphenyl, 4-(N-(t-butoxy-carbonyl)methanesulfonylaminoethanoyl)phenyl, 4-(2-(2-thienylcarboxamido)ethyl)phenyl, thien-2-yl, 5-hydroxy-methylthien-2-yl, 5-formylthien-2-yl, thien-3-yl, 5-hydroxymethylthien-3-yl, 5-formylthien-3-yl, 2-bromothien-3-yl, fur-2-yl, 5-nitrofur-2-yl, fur-3-yl, isoxazol-5-yl, 3-bromoisoxazol-5-yl, isoxazol-3-yl, 5-trimethylsilylisoxazol-3-yl, 5-methylisoxazol-3-yl, 5-hydroxymethylisoxazol-3-yl, 5-methyl-3-phenylisoxazol4-yl, 5-(2-hydroxyethyl)isoxazol-3-yl, 5-acetylisoxazol-3-yl, 5-carboxyisoxazol-3-yl, 5-N-methylcarbamoylisoxazol-3-yl, 5-methoxycarbonylisoxazol-3-yl, 3-bromo[1,2,4]oxadiazol-5-yl, pyrazol-1-yl, thiazol-2-yl, 4-hydroxymethylthiazol-2-yl, 4-methoxycarbonylthiazol-2-yl, 4-carboxythiazol-2-yl, imidazol-1-yl, 2-sulfhydryl-imidazol-1-yl, [1,2,4]triazol-1-yl, tetrazol-5-yl, 2-methyltetrazol-5-yl, 2-ethyltetrazol-5-yl, 2-isopropyl-tetrazol-5-yl, 2-(2-propenyl)tetrazol-5-yl, 2-benzyl-tetrazol-5-yl, pyrid-2-yl, 5-ethoxycarbonylpyrid-2-yl, pyrid-3-yl, 6-chloropyrid-3-yl, pyrid4-yl, 5-trifluoro-methylpyrid-2-yl, 6-chloropyridazin-3-yl, 6-methylpyridazin-3-yl, 6-methoxypyrazin-3-yl, pyrimidin-5-yl, benzothien-2-yl, benzothiazol-2-yl, and quinol-2-yl.

Examples of an unsubstituted or substituted aromatic or heteroaromatic group represented by $R^1$ are unsubstituted or substituted phenyl, furyl, thienyl (such as 3-thienyl) and pyridyl (such as 3-pyridyl).

Examples of an unsubstituted or substituted (5–8C) cycloalkyl group represented by $R^1$ are unsubstituted or substituted cyclopentyl, cyclohexyl, cycloheptyl and cyclooctyl, with cyclohexyl being preferred.

More preferably, $R^1$ represents 2-naphthyl or a group of formula:

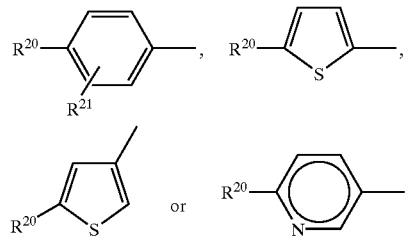

in which $R^{20}$ represents halogen; nitro; cyano; hydroxyimino; (1–10C)alkyl; (2–10C)alkenyl; (2–10C)alkynyl; (3–8C)cyclo-alkyl; hydroxy(3–8C)cycloalkyl; oxo (3–8C)cycloalkyl; halo(1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; tetrazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl-dihydrothiazolyl; (1–4C) alkoxycarbonyldimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; benzothiazolyl; and a group of formula $R^{14}-(L^a)_n-X^2-(L^b)_m$ in which $X^2$ represents a bond, O, NH, S, SO, $SO_2$, CO, CH(OH), CONH, NHCONH, NHCOO, COCONH, $OCH_2CONH$ or CH=CH, NHCO, $L^a$ and $L^b$ each represent (1–4C) alkylene, one of n and m is 0 or 1 and the other is 0, and $R^{14}$ represents a phenyl or hetero-aromatic-group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$, N(CO(1–4C)alkyl)CO, or $NR^{19}COO$, $R^{15}$ represents hydrogen, (1–10C)alkyl, phenyl(1–4C)alkyl, halo (1–10C)alkyl, (1–4C)alkoxycarbonyl(1–4C)alkyl, (1–4C)alkylsulfonylamino(1–4C)alkyl, (1–4C)alkylaminosulfonyl(1–4C)alkyl, (N-(1–4C)alkoxycarbonyl)(1–4C)alkylsulfonylamino(1–4C)alkyl, (3–10C)alkenyl, (3–10C)alkynyl, (3–8C)cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{21}$ represents a hydrogen atom, a halogen atom, a (1–4C)alkyl group or a (1–4C)alkoxy group.

Examples of particular values for $R^{20}$ are fluorine, chlorine, bromine, cyano, hydroxyimino, methyl, ethyl, propyl, 2-propyl, butyl, 2-methylpropyl, 1,1-dimethylethyl, cyclopentyl, cyclohexyl, 3-hydroxycyclopentyl, 3-oxocyclopentyl, methoxy, ethoxy, propoxy, 2-propoxy, acetyl, acetylamino, ethylcarboxamido, propylcarboxamido, 1-butanoylamido, t-butylcarboxamido, acryloylamido, 2-pyrrolidinylcarboxamido, 2-tetrahydrofurylmethoxy, morpholinocarboxamido, methyloxalylamido, cyclopropylcarboxamido, cyclobutylcarboxamido, cyclopentylcarboxamido, cyclohexylcarboxamido, cyclopropylcarbamoyl, cyclopentylcarbamoyl, pyrrolidin-1-yl, morpholino, piperidin-1-yl, N-methylpiperazinyl, N-benzylpiperazinyl, 2-thienyl, 3-thienyl, 2-furyl, 3-furyl, isoxazol-3-yl, thiazol-2-yl, tetrazol-5-yl, pyrid-2-yl, pyrid-3-yl, pyrid-4-yl, pyrimidin-5-yl, 4,5-dihydrothiazol-2-yl, 4,5-dihydro-4-methoxycarbonylthiazol-2-yl, 4,5-dihydro-4-methoxy-carbonyl-5,5-dimethylthiazol-2-yl, benzothien-2-yl, benzothiazol-2-yl, phenyl, 2-fluorophenyl, 3-fluorophenyl, 2,3-difluorophenyl, 4-chlorophenyl, 3,4-dichlorophenyl, 3,5-dichlorophenyl, 3-nitrophenyl, 4-cyanophenyl, 2-methylphenyl, 4-methylphenyl, 4-(4-(1,1-dioxotetrahydro-1,2-thiazinyl)phenyl, 3-trifluoromethylphenyl, 4-trifluoro-methylphenyl, 4-(2-cyanoethenyl, 2-formylphenyl, 3-formylphenyl, 4-formylphenyl, 3-acetyl-phenyl, 4-acetylphenyl, 4-carboxyphenyl, 2-methoxyphenyl, 4-methoxyphenyl, 2-hydroxymethyphenyl, 4-hydroxymethylphenyl, 3-(1-hydroxyethyl)phenyl, 4-(1-hydroxyethyl)phenyl, 4-(1-hydroxypropyl)phenyl, 2-aminophenyl, 4-aminophenyl, 4-N,N-diethylaminophenyl, 4-aminomethylphenyl, 4-(2-aminoethyl)-phenyl, 4-(3-aminopropyl)phenyl, 4-(2-acetylaminoethyl)-phenyl, 4-t-butoxycarboxylaminoethyl)phenyl, 4-(2-t-butoxycarboxylaminoethyl)phenyl, benzylsulfonylamino, 4-isopropylsulfonylaminophenyl, 4-(2-methanesulfonyl-aminoethyl)phenyl, 4-(2-ethylsulfonylaminoethyl)phenyl, 4-(2-propylsulfonylaminoethyl)phenyl, 4-(2-butylsulfonylaminoethyl)phenyl, 4-(2-isopropylsulfonylaminoethyl)phenyl, 4-(1-hydroxy-2-methanesulfonylaminoethyl)phenyl, 4-(2-dimethylaminosulfonylaminoethyl)phenyl, 4-(1-(2-(2-propyl)sulfonylaminopropyl)phenyl, 4-(2-(2,2,2-trifluoro-ethyl)sulfonylaminopropyl)phenyl, 4-(2-cyclohexylsulfonyl-aminoethyl)phenyl, 4-(2-phenylsulfonylaminoethyl)phenyl, 4-(2-(2-fluorophenyl)sulfonylaminoethyl)phenyl, 4-(2-(4-fluorophenyl)sulfonylaminoethyl)phenyl, 4-(2-(2-trifluoromethylphenyl)sulfonylaminoethyl)phenyl, 4-(2-(4-trifluoromethyphenyl)sulfonylaminoethyl)phenyl, 4-(2-(4-methoxyphenyl)sulfonylaminoethyl)phenyl, 4-(2-(1-(5-dimethylamino)napthalenesulfonylamino)ethyl)phenyl, 4-(2-(2-thienyl)sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(2-(2-thienyl-carboxamido)ethyl)phenyl, 4-carbamoylphenyl, 4-methyl-carbamoylphenyl, 4-dimethylcarbamoylphenyl, 4-(2-(2-methylpropaneamido)ethyl)phenyl, 4-(2-(3-methyl-butaneamido)ethyl)phenyl, benzoylmethyl, benzamido, 2-fluorobenzamido, 3-flurobenzamido, 4-fluorobenzamido, 2,4-difluorobenzamido, 3-chlorobenzamido, 4-chlorobenzamido, 4-bromobenzamido, 4-iodobenzamido, 4-cyanobenzamido, 3-methylbenzamido, 4-methylbenzamido, 4-ethylbenzamido, 4-propylbenzamido, 4-t-butylbenzamido, 4-vinylbenzamido, 2-trifluoromethylbenzamido, 3-trifluoromethylbenzamido, 4-trifluoromethylbenzamido, 2-fluoro-4-trifluoromethyl-benzamido, 2-methoxybenzamido, 3-methoxybenzamido, 4-methoxybenzamido, 4-butoxybenzamido, 4-phenylphenyl-carboxamido, 4-benzylcarboxamido, 4-phenoxymethyl-carboxamido, 2-fluorobenzylamino, benzyloxy, 2-fluoro-benzyloxy, 2-hydroxy-2-phenylethyl, 2-fluorophenylcarbamoyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonylamino)ethyl)phenyl, 4-(2-phenylacetamido)-ethyl)phenyl, 4-(methanesulfonylaminoethanoyl)phenyl, 4-(N-t-butoxycarbonyl)methanesulfonylaminoethanoyl)phenyl, 2-thienylcarboxamido, 2-furylcarboxamido, 3-(5-methyl-isoxazolyl)carboxamido, 5-isoxazolylcarboxamido, 2-benzothienylcarboxamido, 4-(5-methyl-3-phenylisoxazolyl)-carboxamido, 4-pyridylcarboxamido, 2-(5-nitrofuryl)-carboxamido, 2-pyridylcarboxamido, 6-chloro-2-pyridyl-carboxamido, 2-thienysulfonamido, 2-thienylmethylamino, 3-thienylmethylamino, 2-furylmethylamino, 3-furylmethylamino, 3-acetylureido and 2-(2-thienyl)ethylureido.

Examples of particular values for $R^{21}$ are hydrogen and chlorine. $R^{21}$ is preferably ortho to $R^{20}$.

Examples of particular values for $R^1$ are 2-naphthyl, 4-bromophenyl, 4-cyanophenyl, 4-benzamidophenyl, 4-methylphenyl, 4-isopropyl-phenyl, 4-isobutylphenyl, 4-t-butylphenyl, 4-methoxyphenyl, 4-isopropoxyphenyl, 4-cyclopentyphenyl, 4-cyclohexylphenyl, 4-(2-hydroxymethylphenyl)phenyl, 4-(4-hydroxymethylphenyl)-phenyl, 4-(2-furyl)phenyl, 4-(3-furyl)phenyl, 4-(2-thienyl)-phenyl, 4-(3-thienyl)phenyl, 4-(pyrrolidin-1-yl)phenyl, 4-(piperidin-I-yl)phenyl, 3-chloro-4-piperidin-1-ylphenyl, 4-benzyloxyphenyl, 4-(2-fluorophenyl)phenyl, 4-(3-fluoro-phenyl)phenyl, 4-(2-formylphenyl)phenyl, 4-(3-formylphenyl)-phenyl, 4-(4-formylphenyl)phenyl, 4-(4-methylphenyl)phenyl, and 4-(2-methoxyphenyl)phenyl.

It is understood that compounds of the formulas If, Ig, and Ih:

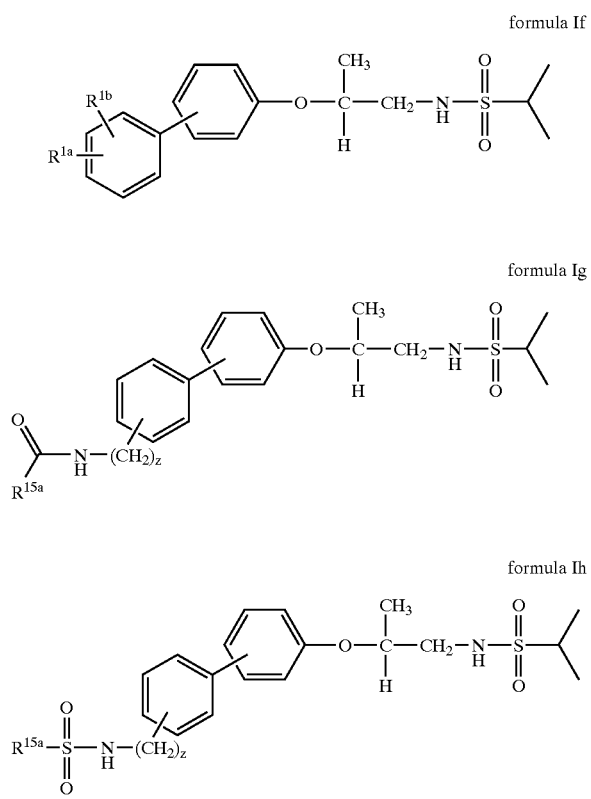

formula If formula Ig formula Ih wherein z is 0, or an integer 1, 2, 3 or 4;

$R^{15a}$ represents (1–6C)alkyl, fluoro(1–4C)alkyl, or phenyl which is unsubstituted or substituted by one or two of halogen, (1–4C)alkyl, halo(1–4C)alkyl, and (1–4C) alkoxy; and $R^{1a}$ and $R^{1b}$ each independently represent hydrogen, halogen; nitro; cyano; (1–10C)alkyl; halo(1–10C)alkyl; phenyl; thienyl; $(CH_2)_z X^3 R^{15b}$ in which z is 0 or an integer 1, 2, 3, or 4, $X^3$ represents O, S, $NR^{16}$, CO, COO, OCO, $R^{15b}$ represents hydrogen, (1–10C)alkyl, phenyl(1–4C)alkyl, halo(1–10C)alkyl, (3–10C) alkenyl, or phenyl which is unsubstituted or substituted by one or two of halogen, (1–4C)alkyl, halo(1–4C) alkyl, di(1–4C)alkylamino and (1–4C)alkoxy; and $R^{16}$ represents hydrogen or (1–10C)alkyl;

or a pharmaceutically acceptable salt thereof;

are included within the scope of the present invention and are particularly preferred.

Preferably, in formula If, $R^{1a}$ is hydrogen and $R^{1b}$ is methyl, methoxy, fluoro, chloro, cyano, $NH_2$, —$CH_2NH_2$, —$CH_2CH_2NH_2$, 2-thienyl, 3-thienyl, —CHO, trifluoromethyl, —$CH_2CN$, —$CO_2CH_3$, or —$CO_2CH_2CH_3$; or $R^{1a}$ and $R^{1b}$ are both hydrogen, fluoro, or chloro.

Preferably, in formulas Ig and Ih, $R^{15a}$ respresents methyl, ethyl, isopropyl, or trifluoromethyl.

Preferably, in formulas Ig and Ih, z represents 0, 1 or 2.

The compounds of formula I can be prepared as set forth in Scheme I. The reagents and starting materials are readily available to one of ordinary skill in the art. All substituents, unless otherwise specified are as previously defined.

Scheme I

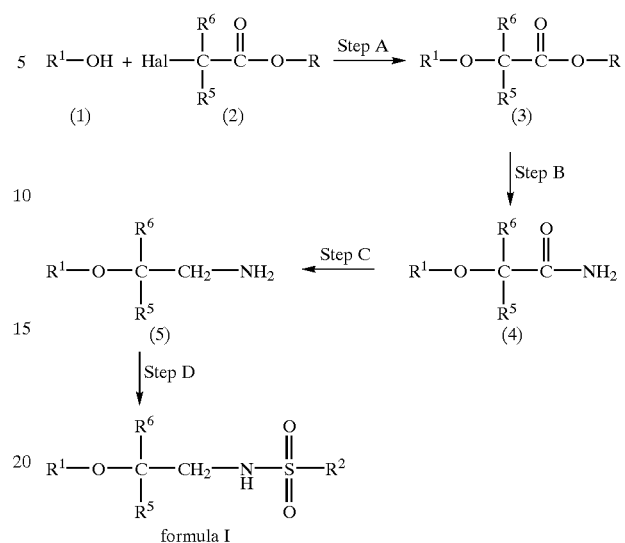

formula I

In Scheme I, step A the compound of structure (1) is O-alkylated with the compound of structure (2). For example, at room temperature, compound (1) is dissolved in a suitable organic solvent, such as N,N-dimethylformamide and added to about 1.0 to about 1.1 equivalents of a suitable base, such as sodium hydride in N,N-dimethylformamide. The reaction mixture is stirred for about 30 minutes to about 2 hours and about one equivalent of compound (2), wherein Hal represents Br or Cl and R represents H or (1–10C)alkyl, dissolved in N,N-dimethylformamide is added dropwise to the reaction mixture. This is followed by addition of about 1.2 equivalents of sodium iodide. The reaction mixture is then heated at reflux for about 2 to 6 hours and then allowed to cool to room temperature. The ether (3) is then isolated and purified by techniques well known in the art, such as extraction techniques and chromatography. For example, the cooled reaction mixture is diluted with water and extracted with a suitable organic solvent, such as ethyl acetate. The organic extracts are combined, washed with water, dried over potassium carbonate, filtered, and concentrated under vacuum to provide the crude ether (3). This crude material is then purified by silica gel chromatography with a suitable eluent, such as hexanelethyl acetate (1:1) to provide the purified ether (3).

In Scheme I, step B, ether (3) is converted to the amide of structure (4) under standard conditions. For example, ether (3) is combined with an excess of ammonia (2M solution of ammonia in methanol for example) in a suitable organic solvent, such as tetrahydrofuran and the reaction mixture is stirred for about 24 to about 48 hours at room temperature. The reaction mixture is then concentrated under vacuum to provide the amide (4).

In Scheme I, step C, the amide (4) is reduced under conditions well known in the art to provide the amine of structure (5). For example, see Jerry March, "Advanced Organic Chemistry," second edition, McGraw-Hill Book Company, 1977, page 1122. More specifically, for example, amide (4) is dissolved in a suitable organic solvent, such as tetrahyrofuran and treated with about 1 equivalent of a suitable reducing agent, such as borane-methyl sulfide complex. The reaction mixture is then heated at reflux for about 8 to 16 hours under a nitrogen atmosphere and then cooled to room temperature. The reaction is then quenched by addition of a tetrahydrofuran/methanol (1:1) mixture until foaming ceases. Then 5N aqueous sodium hydroxide is added and the reaction is heated at reflux for about 5 hours. The reaction is then allowed to cool and is extracted with a suitable organic solvent, such as methylene chloride. The organic extracts are combined, dried over anhydrous sodium sulfate, filtered and concentrated under vacuum to provide the crude amine (5). This material can be converted to its corresponding HCl salt by dissolving the amine (5) in a suitable organic solvent, such as diethyl ether and treating with excess anhydrous HCl gas. The mixture is allowed to stir for about 1 to 6 hours and the resulting precipitate is collected by filtration to provide the amine (5) hydrochloride salt. Alternatively, the mixture can be concentrated under vacuum to provide amine (5) hydrochloride salt.

In Scheme I, step D the amine (5) is sulfonylated under conditions well known in the art with a sulfonyl chloride of formula $ClSO_2R^2$ to provide the compound of formula I. For example, the amine (5) is dissolved in a suitable organic solvent, such as methylene chloride and treated with an excess of a suitable organic base, such as triethylamine under an atmosphere of nitrogen. The solution is cooled to about 0° C. and treated slowly with about 1.0 to 1.2 equivalents of a sulfonyl chloride of formula $ClSO_2R^2$, and the reaction mixture is then allowed to warm to room temperature and stirred for about 8 to 16 hours. The compound of formula I is then isolated and purified by techniques well known in the art. For example, the reaction mixture is quenched with water and the organic phase is separated from the aqueous layer. The organic phase is then dried over anhydrous sodium sulfate, filtered, and concentrated under vacuum to provide the crude compound of formula I. This crude material is then purified by silica gel chromatography with a suitable eluent, such as hexane/ethyl acetate (1:1) to provide the purified compound of formula I.

The compounds of formula I in which $R^1$ represents a 4-bromophenyl group may be converted into other compounds of formula I in which $R^1$ represents a 4-substituted alkyl- or cycloalkylphenyl group, such as 4-cyclopentylphenyl by treatment of the corresponding bromide with an appropriate alkyl- or cycloalkyl Grignard reagent, such as cyclopentyl-magnesium bromide, in the presence of a palladium(II) catalyst, such as [1,1'-bis(diphenylphosphino)ferrocene]-dichloropalladium(II) ($PdCl_2(dppf)$), in an aprotic solvent, such as diethyl ether at temperatures ranging from −78° C. to 25° C.

Alternatively, the compounds of formula I in which $R^1$ represents a 4-bromophenyl group may be converted to a 4-(trimethylstannyl)phenyl or 4-(tri-n-butylstannyl)phenyl group by treatment of the corresponding bromide with a palladium(0) catalyst, such as tetrakis(triphenylphosphine)-palladium(0) and hexaalkyldistannane, where the alkyl group is methyl or n-butyl, in an aprotic solvent such as toluene in the presence of a tertiary amine base such as triethyl-amine, at temperatures ranging from 80 to 140° C., preferably from 90 to 110° C.

The compounds of formula I in which $R^1$ represents a 4-(tri-n-butylstannyl)phenyl group may then be reacted with an aryl- or heteroarylbromide, such as 2-bromothiophene-5-carboxaldehyde, or an aryl- or heteroaryliodide, or an aryl- or heteroaryltriflate, in the presence of a palladium(0) catalyst, such as tetrakis(triphenylphosphine)palladium(0), or a palladium(II) catalyst, such as bis(triphenylphosphine)-palladium(II) dichloride, in an aprotic solvent, such as dioxane, at temperatures ranging from 80 to 140° C., preferably from 90 to 110° C., to afford the corresponding 4-(aryl)phenyl or 4-(heteroaryl)phenyl substituted compound.

The compounds of formula I in which $R^1$ represents a 4-bromophenyl group may be converted into a 4-substituted carboxyaldehydephenyl(formylphenyl) group by reaction of the corresponding bromide with the carbon monoxide gas which is bubbled into the reaction under atmospheric pressure in the presence of a palladium(II) catalyst, such as bis(triphenyl-phosphine)palladium(II) dichloride and sodium formate in an aprotic solvent, such as dimethylformamide at temperatures ranging from 70 to 110° C., preferably at 90° C.

The compounds of formula I in which $R^1$ represents a 4-hydroxyphenyl group may be converted into other compounds of formula I in which $R^1$ represents an alkoxy group by treatment of the corresponding hydroxyphenyl group with an appropriate alkyl halide such as benzyl bromide in the presence of sodium hydride in an aprotic solvent such as dimethylformamide at temperatures ranging from 25 to 100° C., preferably from 50 to 90° C.

More specifically, the compounds of formulas Ia and Ib can be prepared as set forth in Scheme II. The reagents and starting materials are readily available to one of ordinary skill in the art. All substituents, unless otherwise specified are as previously defined.

Scheme II

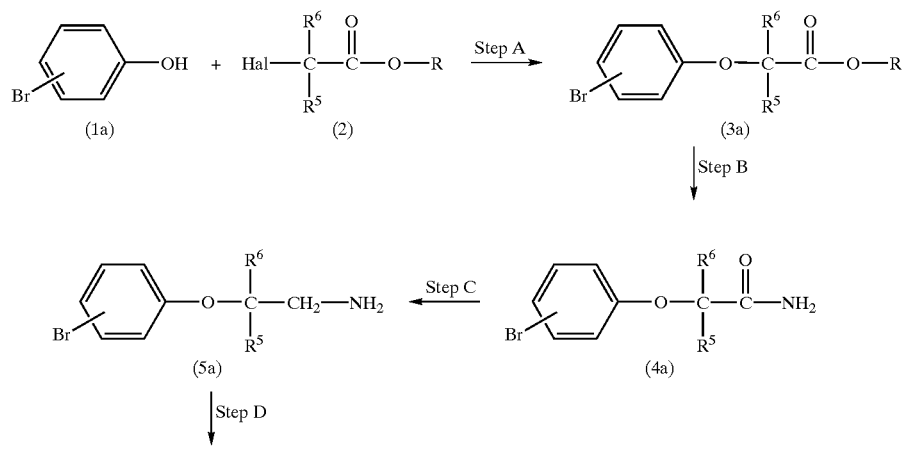

-continued

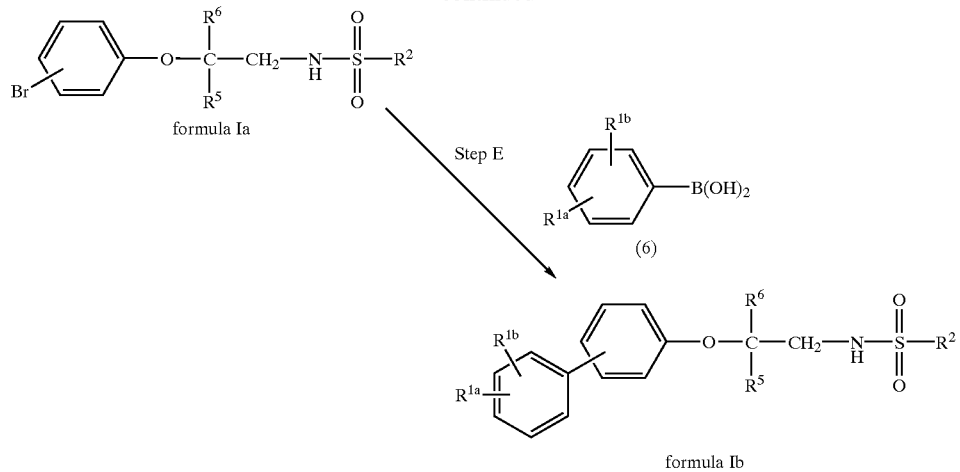

formula Ia

Step E (6)

formula Ib

In Scheme II, step A the compound of structure (1a) is O-alkylated with the compound of structure (2) to provide the ether of structure (3a) in a manner analogous to the procedure set forth above in Scheme I, step A.

In Scheme II, step B, ether (3a) is converted to the amide of structure (4a) in a manner analogous to the procedure set forth above in Scheme I, step B.

In Scheme II, step C, the amide (4a) is reduced in a manner analogous to the procedure described in Scheme I, step C above, to provide the amine of structure (5a).

In Scheme II, step D the amine (5a) is sulfonylated with a sulfonyl chloride of formula $ClSO_2R^2$ to provide the compound of formula Ia in a manner analogous to the procedure set forth in Scheme I, step D above.

In Scheme II, step E, the compound of formula Ia is coupled with the boronic acid of structure (6), wherein $R^{1a}$ and $R^{1b}$ each independently represent hydrogen, halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; thienyl; $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C) alkyl, phenyl(1–4C)alkyl, halo(1–10C)alkyl, (1–4C) alkoxycarbonyl(1–4C)alkyl, (1–4C)alkylsulfonylamino (1–4C)alkyl, (N-(1–4C)alkoxycarbonyl)(1–4C) alkylsulfonylamino(1–4C)alkyl, (3–10C)alkenyl, (3–10C) alkynyl, (3–8C)cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; under conditions well known in the art to provide the biphenyl compound of formula Ib. For example, see International Patent Application Publication: WO 98/33496 published Aug. 6, 1998. More specifically, for example, the compound of formula Ia is combined with about 1.0 to about 1.2 equivalents of a boronic acid (6), a catalytic amount of tetrakis (triphenylphosphine)palladium(0), and an excess of a suitable base, such as aqueous sodium carbonate, in a suitable organic solvent, such as 1,4-dioxane under an atmosphere of nitrogen. The reaction mixture is heated at reflux for about 8 to about 16 hours. After cooling, the reaction is then quenched with water and the compound of formula Ib is isolated and purified by techniques well known in the art, such as extraction techniques and silica gel chromatography respectively. For example, the quenched reaction is extracted with a suitable organic solvent, such as methylene chloride, the organic extracts are combined, dried over anhydrous sodium sulfate, filtered, and concentrated under vacuum to provide crude compound of formula Ib. This crude material is then purified by silica gel chromatography with a suitable eluent, such as hexane/ethyl acetate (1:1) to provide the purified compound of formula Ib.

Alternatively, in Scheme II, step E, the compound of formula Ia is combined with about 1.1 to about 1.2 equivalents of a boronic acid (6), a catalytic amount of dichlorobis (triphenylphosphine)palladium (II), and an excess of a suitable base, such as aqueous sodium carbonate, in a suitable organic solvent, such as 1,2-dimethoxyethane under an atmosphere of nitrogen. The reaction mixture is heated at reflux for about 8 to about 16 hours. After cooling, the reaction is then quenched with water and the compound of formula Ib is isolated and purified by techniques well known in the art, such as extraction techniques and silica gel chromatography respectively. For example, the quenched reaction is extracted with a suitable organic solvent, such as methylene chloride, the organic extracts are combined, dried over anhydrous magnesium sulfate, filtered, and concentrated under vacuum to provide crude compound of formula Ib. This crude material is then purified by silica gel chromatography with a suitable eluent, such as hexane/ethyl acetate (1:1) to provide the purified compound of formula Ib.

Alternatively, the coupling reaction may be carried out using palladium diacetate with a suitable organic solvent, such as n-propanol or acetone. See for example, *Organic Synthesis* 1998, 75, 61; Goodson, F. E.; Wallow, T. I.; Novak, B. M. and *Organic Synthesis* 1998, 75, 53; Huff, B. E.; Koenig, T. M.; Mitchell, D.; Staszak, M. A. wherein analogous coupling conditions are employed.

The boronic acid (6) may be prepared, for example, by reacting a trialkyl borate, such as triisopropyl borate with an appropriate organolithium compound at reduced temperature. For example, 2-fluorobenzeneboronic acid may be prepared by reacting 2-fluorobromobenzene with butyllithium in tetrahydrofuran at about −78° C. to afford 2-fluorophenyl lithium, and then reacting this organolithium compound with triisopropyl borate. This is followed by hydrolysis with aqueous HCl.

The compounds of formulas Ic, Id, and Ie can be prepared as set forth in Scheme III. The reagents and starting materials are readily available to one of ordinary skill in the art. All substituents, unless otherwise specified are as previously defined.

Scheme III

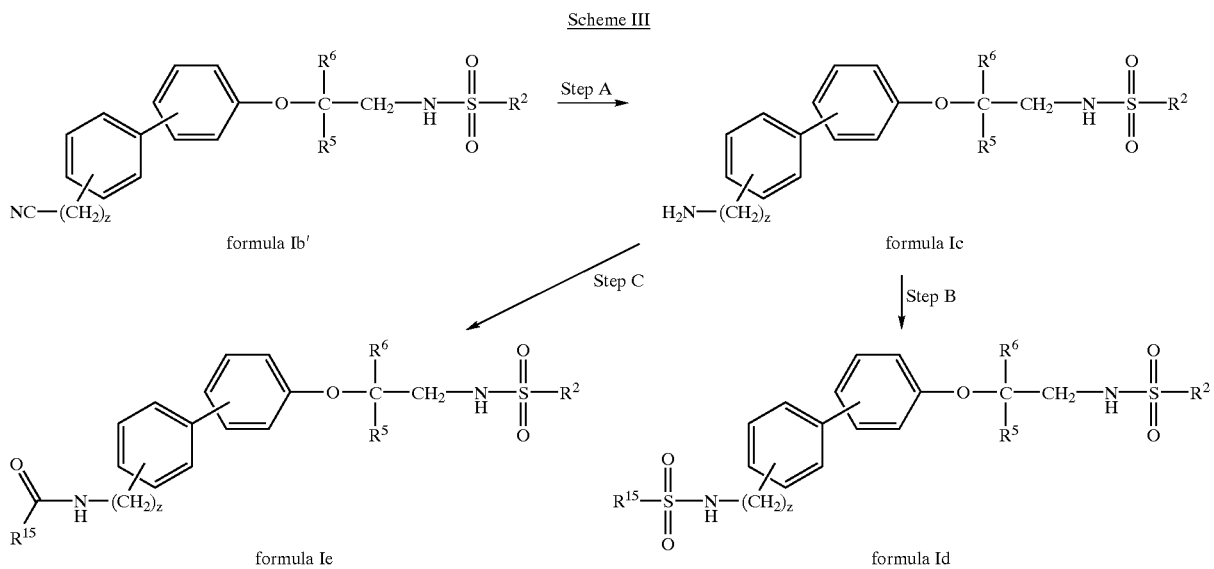

In Scheme III, step A, the compound of formula Ib' wherein z is 0 or an integer 1, 2, 3 or 4, is reduced to the amine of formula Ic under conditions well known in the art. For example, see Jerry March, "Advanced Organic Chemistry," second edition, McGraw-Hill Book Company, 1977, page 835. More specifically, for example, compounds of formula Ib' are dissolved in a suitable organic solvent, such as tetrahydrofuran and treated with an excess of a suitable reducing agent, such as borane-methyl sulfide complex. The reaction mixture is then heated at reflux for about 8 to 16 hours, and then allowed to cool to room temperature. The reaction is treated with a mixture of tetrahydrofuran/methanol (1:1) until foaming ceases. The reaction is then treated with 5N aqueous sodium hydroxide and heated at reflux for about 3 to 6 hours. The reaction is then cooled to room temperature and extracted with a suitable organic solvent, such as methylene chloride. The organic extracts are combined, dried over potassium carbonate, filtered, and concentrated under vacuum to provide the crude amine of formula Ic. The crude material is then purified by techniques well known in the art, such as silica gel chromatography or formation of the corresponding HCl salt and subsequent crystallization. For example, the crude amine of formula Ic is dissolved in a suitable organic solvent, such as diethyl ether and treated with excess anhydrous HCl gas. The mixture is allowed to stir for about 1 to 3 hours and the resulting precipitate is collected by filtration. The precipitate is washed with cold diethyl ether and dried under vacuum to provide the purified amine HCl salt of formula Ic.

In Scheme III, step B the amine of formula Ic is sulfonylated under standard conditions with a sulfonyl chloride of formula $ClSO_2R^{15}$, wherein $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl) (1–4C)alkylsulfonylamino(1–4C)alkyl, (3–10C)alkenyl, (3–10C)alkynyl, (3–8C)cycloalkyl, camphoryl or an aromatic or heteroaromatic group which is unsubstituted or substituted by one or two of halogen, (1–4C)alkyl, halo (1–4C)alkyl, di(1–4C)alkylamino and (1–4C)alkoxy, to provide the compound of formula Id. For example, the amine of formula Ic is dissolved in a suitable organic solvent, such as methylene chloride under an atmosphere of nitrogen, and treated with an excess of a suitable organic base, such as triethylamine. The solution is cooled to about 0° C. and treated with about 1.1 to about 1.5 equivalents of a sulfonyl chloride of formula $ClSO_2R^{15}$. After addition is complete, the reaction mixture is allowed to warm to room temperature and stirred for about 8 to 16 hours. The reaction is then quenched with water, the organic layer is separated, dried over anhydrous sodium sulfate, filtered, and concentrated under vacuum to provide the crude compound of formula Id. This crude material is purified by silica gel chromatography with a suitable eluent, such as ethyl acetate/hexane (1:1) to provide the purified compound of formula Id.

In Scheme III, step C the amine of formula Ic is converted to the amide of formula Ie under conditions well known in the art. For example, amide formation can be carried out using standard peptide coupling procedures well known in the art, such as the azide method, the mixed carbonic acid anhydride (isobutyl chloroformate) method, or the carbodiimide (dicyclohexylcarbodiimide, diisopropylcarbodiimide, or water-soluble carbodiimide) method. Some of these methods, such as the carbodiimide method, can be enhanced by adding 1-hydroxybenzotriazole. More specifically, for example, the amine of formula Ic is dissolved in a suitable organic solvent, such as methylene chloride under an atmosphere of nitrogen, and treated with an excess of a suitable organic base, such as triethylamine. The solution is cooled to about 0° C. and treated with about 1.1 to about 1.5 equivalents of an acid chloride of formula $ClCOR^{15}$. After addition, the reaction mixture is allowed to warm to room temperature and stirred for about 8 to 16 hours. The reaction is then quenched with water and dried over anhydrous sodium sulfate, filtered, and concentrated under vacuum to provide the crude amide of formula Ie. This crude material is purified by silica gel chromatography with a suitable eluent, such as ethyl acetate/hexane (1:1) to provide the purified compound of formula Ie.

The following examples further illustrate the invention and represent typical syntheses of the compounds of formula I as described generally above. The reagents and starting materials are readily available to one of ordinary skill in the art. As used herein the term "Chromatotron®" (Harrison Research Inc., 840 Moana Court, Palo Alto Calif. 94306) is recognized by one of ordinary skill in the art as an instrument which is used to perform centrifugal thin-layer chromatography. As used herein, the following terms have the meanings indicated: "eq" refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "EtOAc" refers to ethyl acetate; "aq" refers to aqueous; "iPrOAc" refers to isopropyl acetate; "MTBE" refers to tert-butyl methyl ether; "methyl DAST" refers to dimethylaminosulfur trifluoride, "DAST" refers to diethylaminosulfur trifluoride, "DBU" refers to 1,8-diazabicyclo[5.4.0]undec-7-ene; as used herein "Pd(dppf)$_2$Cl$_2$ catalyst" refers to ([1,1'-bis(diphenylphosphino)ferrocene]dichloropalladium(II) complex with CH$_2$Cl$_2$; as used herein the terms "Me", "Et", "Pr", "iPr", and "Bu" refer to methyl, ethyl, propyl, isopropyl, and butyl respectively, and "RT" refers to room temperature.

EXAMPLE 1

Preparation of [2-(4-Bromophenoxy)propyl][(methylethyl)sulfonyl]amine.

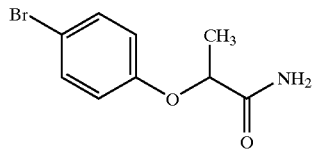

Preparation of Methyl 2-(4-bromophenoxy)propanoate.

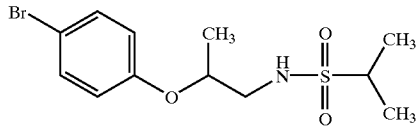

Scheme I or II, step A: In a 3 L round-bottomed flask fitted with a stir bar, at room temperature, and under a nitrogen atmosphere, 4-bromophenol (50.0 g, 289 mmol) in 290 mL of N-N-dimethylformamide was added dropwise to sodium hydride (7.6 g, 317 mmol) in 290 mL of N-N-dimethylformamide. After mixing for 45 minutes, 2-bromopropionate (47.0 g, 290 mmol) in 290 mL of N-N-dimethylformamide was added dropwise from an addition funnel, and was followed with the addition of sodium iodide (52.0 g, 347 mmol, neat). The reaction mixture was then brought to reflux at 80° C. for 3 hours. The reaction mixture was allowed to cool to room temperature, whereby it was diluted with 1.6 L H$_2$O, and extracted three times with 500 mL of ethyl acetate. The organic layer was washed two times with 500 mL of H$_2$O, dried with potassium carbonate, filtered, and concentrated under reduced vacuum to yield 81.8 g of viscous brown oil. This crude material was purified via silica gel chromatography, employing a Hewlett-Packard HPLC 2000 and eluting with a 1:1 hexane:ethyl acetate solvent system to yield the intermediate title compound (37.0 g, 49%) as a viscous oil. Electrospray-MS 260, d (M*+1), Preparation of 2-(4-Bromophenoxy)propanamide.

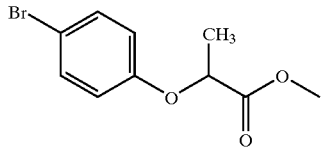

Scheme I or II, step B: Methyl 2-(4-bromophenoxy)propanoate (37.01 g, 143 mmol), ammonia (1.86 L of a 2M solution in methanol) and tetrahydrofuran (475 mL) were combined in a 3 L round bottom flask at room temperature, under a nitrogen atmosphere, and stirred by stirbar, for 48 hours. Upon completion, the reaction mixture was concentrated under reduced pressure to yield the intermediate title compound (35.9 g, 100%) as a viscous oil. Electrospray-MS 245, d (M*+1).

Preparation of Final Title Compound.

Scheme I or II, steps C and D: In a 1000 mL 3-neck flask, fitted with a thermometer, a stirbar and a condenser, 2-(4-bromophenoxy)propanamide (6.7 g, 27.4 mmol) was combined with borane-methyl sulfide complex (27.5 mL of a 10 M concentration in excess methyl sulfide), and tetrahydrofuran (330 mL). The is reaction mixture was heated at reflux with stirring, at 70° C., overnight, under a nitrogen atmosphere. The reaction mixture was allowed to cool to room temperature and 82.4 mL of 1:1 tetrahydrofuran methyl alcohol was added dropwise, slowly, until foaming ceased. Next, 5N sodium hydroxide (257 mL) was added, and the reaction mixture was refluxed for 5 hours. The mixture was then permitted to cool to room temperature and extracted three times with 200 mL methylene chloride. The organic layer was dried with anhydrous sodium sulfate, filtered, and concentrated under reduced vacuum, yielding 5.3 g of viscous purple oil. This oil was dissolved in diethyl ether, and acidified with anhydrous hydrochloric acid gas (until precipitation occurred). The acid mixture was allowed to stir at room temperature for 1 hr, forming a white precipitate. The precipitate was captured by vacuum filtration yielding 4.4 g of white solid. The precipitate was then dissolved into methylene chloride (185 mL) and added to triethylamine (10 mL, 69 mmol) in a 500 mL 3-neck flask fitted with a thermometer under a nitrogen atmosphere. The mixture was then cooled to 0° C. and 2-propanesulfonyl chloride (5.0 mL, 41 mmol) was added by syringe. The mixture was permitted to come to room temperature, and stirred overnight, under a nitrogen system. The reaction was quenched with excess water, and the organic layer was dried with anhydrous sodium sulfate, filtered, and concentrated under vacuum, yielding 5.03 g viscous oil. Purification was conducted using a Hewlett-Packard HPLC 2000, with two silica cartridges, and eluting with a 1:1 hexane:ethyl acetate solvent system, yielding the final title compound (3.5 g, 38%) as a slow crystallizing, yellow viscous oil. Electrospray-MS 337, d (M*+1).

Analysis

Theory: C 42.87, H 5.40, N 4.16.
Found: C 42.82, H 5.38, N 4.12.

EXAMPLE 1A

Preparation of [(2S)-2-(4-bromophenoxy)propyl][(methylethyl)sulfonyl]amine.

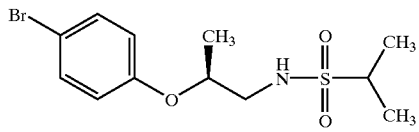

Preparation of (2S)-2-(4-bromophenoxy)propanoic acid.

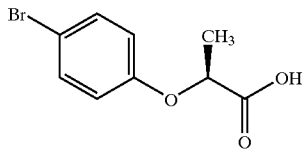

Scheme II, step A: To a mixture of sodium hydride (54.92 g, 1.37 moles) and THF (500.0 ml) at reflux was added a solution of 4-bromophenol (47.6 g, 0.275 moles) dissolved in THF (200.0 ml) over a period of 60.0 minutes (vigorous gas evolution is observed which can be controlled by the rate of substrate addition). The reaction is then heated at reflux until no gas evolution is observed. Then neat (S)α-chloropropionic acid (59.72 g, 0.550 moles) is added very carefully over a period of 60.0 minutes (gas evolution can be controlled by the rate of addition). The reaction is then heated at reflux for 120.0 minutes, then quenched with deionized water (1000.0 ml) at reflux very carefully. The reaction is then allowed to equilibrate to room temperature and the organic extracted with methylene chloride (1400.0 ml). To the aqueous layer, which contains the sodium salt of the product, is then added fresh methylene chloride (700.0 ml) and the mixture is acidified with 6N HCl (180.0 ml) very carefully at room temperature. The lower organic layer is then separated and subsequently dried with anhydrous magnesium sulfate, filtered, and solvent exchanged with hexane under reduced pressure to to afford an off tan precipitate of the intermediate title compound, (65.06 g, 96.4%); $^1$H nmr (CDCl$_3$) δ 1.65–1.66 (d, 3H, J=6.83 Hz), 4.72–4.76 (m, 1H), 6.76–6.78 (d, 2H, J=9.03 Hz), 7.37–7.39 (d, 2H, J=9.03), 11.0; $^{13}$C nmr (CDCl$_3$) δ 18.61, 72.40, 114.43, 117.15, 132.75, 156.57, 178.31).

Preparation of (2S)-2-(4-bromophenoxy)propanamide.

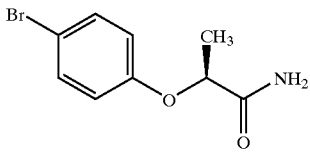

Scheme II, step B: To a solution of (2S)-2-(4-bromophenoxy)propanoic acid (prepared above) and THF (300.0 ml) at room temperature was added (N-methylmorholine) NMM (11.02 ml) immediately followed by (Chlorodimethoxytriazine) CDMT (17.6 g). After 45 minutes of stirring, NMM (17.64 ml) and ammonium chloride (8.04 g) was added to the reaction mixture. The reaction was then capped and stirred for 24.0 hours. Filtration of the precipitated solid and concentration of the filtrate under reduced pressure afforded an oil. To the oil was then added methylene chloride (150.0 ml) and 1N HCl (200.0 ml) with vigorous stirring. The organic layer was then separated, dried with anhydrous magnesium sulfate, filtered, and subsequently solvent exchanged with hexane to afford a tan precipitate. The precipitate was then dried in a house vacuum at 50° C. to provide the intermediate title compound (18.93 g, 77.4%); $^1$H nmr (CDCl$_3$) δ 1.56–1.58 (d, 3H, J=6.83Hz), 4.6 (m, 1H), 5.58 (b, 1H), 6.47 (b, 1H), 6.78–6.81 (d, 2H, J=9.03 Hz), 7.40–7.42 (d, 2H, J=9.03 Hz).

Preparation of (2S)-2-(4-bromophenoxy)propylamine.

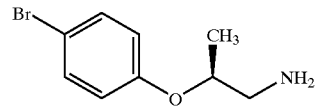

Scheme II, step C: To a solution of (2S)-2-(4-bromophenoxy)propanamide (18.93 g, 77.93 mmoles) and THF (300.0 ml) at room temperature was added 10M solution of borane dimethylsufide (23.42 ml, 233.8 mmoles) over a period of 20 minutes. The reaction exothermed with evolution of gas. It was heated at reflux for 4.5 hours then quenched very carefully with 4N HCl in Dioxane solution over a period of 30.0 minutes (caution: evolution of gas). The reaction was stirred for 10.0 minutes, then ethanol (105.7 ml) was added very carefully over a period of 30.0 minutes. The reaction was concentrated to a constant weight of a white slurry (54.0 g). To the slurry was then added toluene (200.0 ml) followed by azeotropic removal of low boiling solvents to a white slurry, followed by addition of ethyl acetate (100.0 ml) and ethyl ether (100.0 ml). Vigorous stirring of the reaction mixture, filtration, and subsequent drying under a house vacuum at 45° C. for 18.0 hours afforded the intermediate title compound (13.0 g, 63%) as a white precipitate; $^1$H nmr (DMSO) δ 1.21–1.22 (d, 3H, J=6.1 Hz), 2.90–2.98 (m, 1H), 3.03–3.05 (m, 1H), 4.67–4.70 (m, 1H), 6.96–6.98 (d, 2H, J=9.03 Hz), 7.43–7.45 (d, 2H, J=9.03 Hz); 13C nmr (DMSO) δ 17.48, 43.75, 71.63, 113.37, 119.26, 132.88, 156.82).

Preparation of Final Title Compound.

Scheme II, step D: To a reaction mixture of (2S)-2-(4-bromophenoxy)propylamine (19.0 g, 71.275 mmoles) and methylene chloride (200.0 ml) at room temperature was added 2N NaOH (150.0 ml) all at once with vigorous stirring for 45 minutes. The organic layer was separated, dried anhydrous magnesium sulfate, filtered, and the filtrate concentrated to an oil (16.22 g). To a solution of this oil in methylene chloride (225.0 ml) at room temperature was then added triethylamine (23.6 ml, 169.23 mmol) and N,N-dimethylaminopyridine (0.43 g) with stirring. The solution was cooled to −20° C. with dry ice/acetone bath, and a solution of isopropylsulfonyl chloride (9.5 ml, 84.62 mmol) dissolved in methylene chloride (25 ml) was added over a period of 30 minutes while maintaining the temperature at −20° C. The reaction was then stirred to room temperature overnight. The reaction was monitored with TLC (1:1 ethylacetate/hexane) until the reaction was complete. The reaction was quenched with 3N HCl solution (100.0 ml), the organic layer separated then dried with anhydrous magnesium sulfate. Subsequent filtration and concentration at reduced pressure afforded the final title compound (23.7 g, 100%) as an oil; $^1$H nmr (CDCl$_3$) δ 1.25–1.26 (d, 3H, J=6.35 Hz), 1.33–1.35 (d, 6H, J=6.83 Hz), 3.14–3.19 (m, 1H), 3.22–3.26 (m, 1H), 3.34–3.36 (m, 1H), 4.43–4.46 (m, 1H), 4.74–4.76 (m, NH), 6.77–6.79 (d, 2H, J=9.03 Hz), 7.35–7.37 (d, 2H, J=9.03 Hz); $^{13}$C nmr (CDCl$_3$) δ 16.91, 48.59, 53.94, 74.13, 113.84, 118.09, 132.72, 156.51).

EXAMPLE 1B
Preparation of [(2R)-2-(4-bromophenoxy)propyl][(methylethyl)sulfonyl]amine.

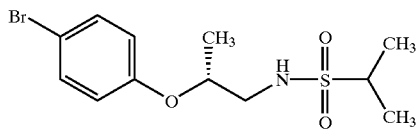

The title compound can be prepared from (R)-2-chloroproprionic acid in a manner analogous to the the procedure set forth in example 1A.

EXAMPLE 2
Preparation of [(Methylethyl)sulfonyl]{2-[4-(4-(3-thienyl)phenoxy]propyl}amine.

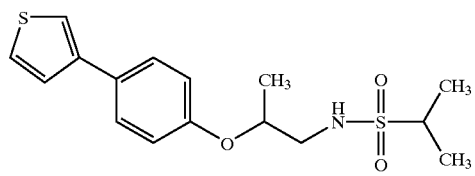

Scheme II, step E: [2-(4-Bromophenoxy)propyl][(methylethyl)sulfonyl]amine (260 mg, 0.773 mmol, prepared in example 1), thiophene-3-boronic acid (120 mg, 0.938 mmol), tetrakis(triphenylphosphine)palladium(0) (5 mg, 0.004 mmol), sodium carbonate (276 mg in 1.3 mL water) and 1,4-dioxane (5 mL) were combined in a 15 mL round bottom flask, fitted with a condenser, stirbar, and in a temperature regulated oil bath. The reaction mixture was heated at reflux (70° C.) under a nitrogen atmosphere overnight. The reaction was quenched with water, extracted three times with 25 mL of methylene chloride, and the organic layer dried with anhydrous sodium sulfate, filtered, and concentrated under reduced pressure, yielding 230 mg brown viscous oil. This material was purified via silica gel chromatography, utilizing a Chromatotron® (the Chromatotron® is available from Harrison Research Inc., 840 Moana Court, Palo Alto Calif. 94306) with a 2000 μm rotor utilizing an eluent of 1:1 hexane:ethyl acetate, yielding the title compound (126 mg, 48.4%), Electrospray-MS 340.0 (M*+1).
Analysis
Theory: C 56.61, H 6.24, N 4.13.
Found: C 56.41, H 6.12, N 4.11.

EXAMPLE 3
Preparation of {2-[4-(3-Aminophenyl)phenoxy]propyl}[(methylethyl)sulfonyl]amine.

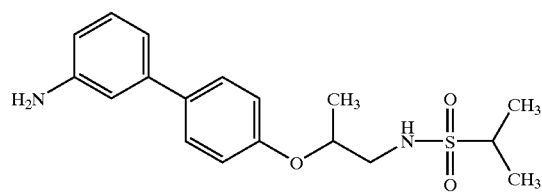

Scheme II, step E: The title compound (230 mg, 82%) was prepared from [2-(4-bromophenoxy)propyl][(methylethyl)sulfonyl]amine (270 mg, 0.803 mmol, prepared in example 1), 3-aminobenzeneboronic acid monohydrate (150 mg, 0.968 mmol), tetrakis(triphenylphosphine)palladium(0) (5 mg, 0.004 mmol), 2 M sodium carbonate (290 mg in 1.4 mL water) and 1,4-dioxane (5.5 mL) in a manner analogous to the procedure described in Example 2.
Electrospray-MS 347.2 (M*−1).

EXAMPLE 4
Prepation of [(Methylethyl)sulfonyl][2-(4-phenylphenoxy)propyl]amine.

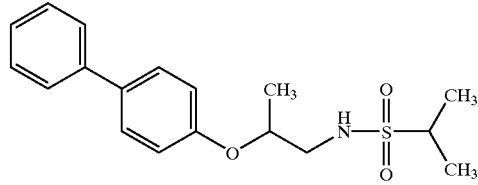

Scheme II, step E: The title compound (290 mg, 48.4%) was prepared from [2-(4-bromophenoxy)propyl][(methylethyl)sulfonyl]amine (450 mg, 1.34 mmol, prepared in example 1), benzeneboronic acid (200 mg, 1.64 mmol), tetrakis(triphenylphosphine)palladium(0) (8.5 mg, 0.007 mmol), 2 M sodium carbonate (480 mg in 2.3 mL water) and 1,4-dioxane (9 mL) in a manner analogous to the procedure described in Example 2.
Electrospray-MS 334.0 (M*+1).

EXAMPLE 5
Preparation of {2-[4-(2-Chlorophenyl)phenoxy]propyl}[(methylethyl)sulfonyl]amine.

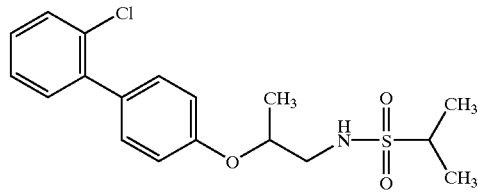

Scheme II, step E: The title compound (125 mg, 38%) was prepared from [2-(4-bromophenoxy)propyl][(methylethyl)sulfonyl]amine (300 mg, 0.89 mmol, prepared in example 1), 2-chlorobenzeneboronic acid (170 mg, 1.09 mmol), tetrakis(triphenylphosphine)palladium(0) (5.6 mg, 0.005 mmol), 2 M sodium carbonate (320 mg in 1.5 mL water) and 1,4-dioxane (9 mL) in a manner analogous to the procedure described in Example 2.
Electrospray-MS 368.0 (M*+1).

EXAMPLE 6
Preparation of [(Methylethyl)sulfonyl]{2-[4-(3-methylphenyl)phenoxy]propyl}amine.

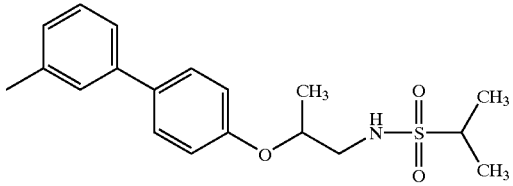

Scheme II, step E: The title compound (18 mg, 6%, white foam) was prepared from [2-(4-bromophenoxy)propyl][(methylethyl)sulfonyl]amine (275 mg, 0.818 mmol, prepared in example 1), 3-methylbenzeneboronic acid (135 mg, 0.993 mmol), tetrakis(triphenylphosphine)palladium(0) (15 mg, 0.013 mmol), 2 M sodium carbonate (295 mg in 1.4 mL water) and 1,4-dioxane (5.5 mL) was prepared in a manner analogous to the procedure described in Example 2. The crude material was purified utilizing a Chromatotron® with a 2000 μm rotor in a 1:1 hexane:ethyl acetate solvent system, yielding 110 mg of a co-eluting mixture of unreacted starting material and title compound. This mixture was further purified by reverse phase, chromatography on a Vydac C-18 column in a gradient of 5 to 70% of 0.1% trifluoroacetic acidlacetonitrile in water over 45 minutes at 200 mL/min elution rate.
Electrospray-MS 348.0 (M*+1).

EXAMPLE 7
Preparation of {2-[4-(4-Chlorophenyl)phenoxy]propyl}[(methylethyl)sulfonyl]amine.

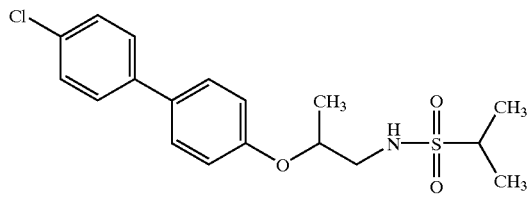

Scheme II, step E: The title compound (10.9 mg, 3.2%, white foam) was prepared from [2-(4-bromophenoxy)propyl][(methylethyl)sulfonyl]amine (270 mg, 0.803 mmol, prepared in example 1), 4-chlorobenzeneboronic acid (151 mg, 0.966 mmol), tetrakis(triphenylphosphine)palladium(0) (15 mg, 0.013 mmol), 2 M sodium carbonate (295 mg in 1.4 mL water) and 1,4-dioxane (5.5 mL) in a manner analogous to the procedure described in Example 2. The crude material was purified utilizing a Chromatotron® with a 2000 μm rotor in a 1:1 hexane:ethyl acetate solvent system, yielding 115 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.
Electrospray-MS 369.0 (M*+1).

EXAMPLE 8
Preparation of {2-[4-(3-Chlorophenyl)phenoxy]propyl}[(methylethyl)sulfonyl]amine.

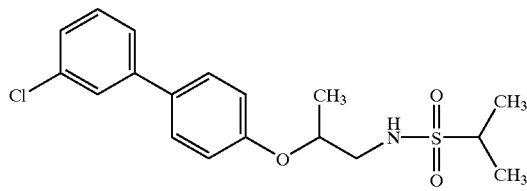

Scheme II, step E: [2-(4-Bromophenoxy)propyl][(methylethyl)sulfonyl]amine (300 mg, 0.892 mmol, prepared in example 1), 3-chlorobenzeneboronic acid (170 mg, 1.09 mmol), dichlorobis(triphenylphosphine)palladium(II) (25 mg, 0.036 mmol), 2 M sodium carbonate (320 mg in 1.5 mL water) and 1,2-dimethoxyethane (6.0 mL) were combined in a 15 ml round bottom flask, fitted with a condenser, stirbar, and in a temperature regulated oil bath, and heated at reflux 85 C. in a nitrogen system overnight. The reaction mixture was quenched with water and extracted three times with 25 mL of methylene chloride. The organic extracts were combined, dried over anyhydrous magnesium sulfate, filtered, and concentrated under reduced pressure, yielding 190 mg brown viscous oil. This material was purified via silica gel chromatography, utilizing a Chromatotron® with a 2000 μm rotor in a 1:1 hexane:ethyl acetate solvent system, yielding the title compound (175 mg, 53%) as a yellow foam. Electrospray-MS 369.0 (M*+1).

EXAMPLE 9
Preparation of [(Methylethyl)sulfonyl]{2-[4-(2-methylphenyl)phenoxy]propyl}amine.

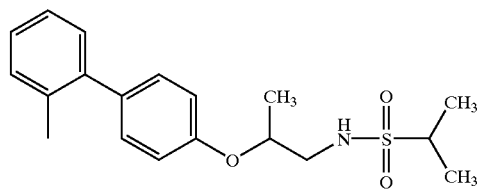

Scheme II, step E: The title compound (120 mg, 34%, yellow foam) was prepared from [2-(4-bromophenoxy)propyl][(methylethyl)sulfonyl]amine (343 mg, 1.02 mmol, prepared in example 1), 2-methylbenzeneboronic acid (165 mg, 1.21 mmol), dichlorobis(triphenylphosphine)palladium (II) (30 mg, 0.043 mmol), 2 M sodium carbonate (370 mg in 1.75 mL water), and 1,2-dimethoxyethane (6.8 mL) in a manner analogous to the procedure described in Example 8.
Electrospray-MS 348.0 (M*+1).

EXAMPLE 10
Preparation of [(Methylethyl)sulfonyl]{2-[4-(3-(2-thienyl)phenyl)phenoxy]propyl}amine.

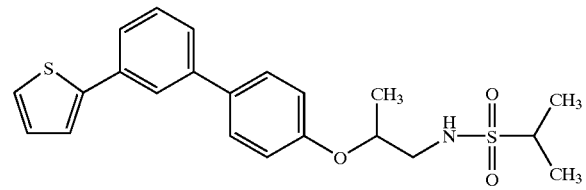

Scheme II, step E: The title compound (243 mg, 77.6%, yellow foam) was prepared from [2-(4-Bromophenoxy)propyl][(methylethyl)sulfonyl]amine (310 mg, 0.922 mmol, prepared in example 1), 3-(2-thienyl)benzeneboronic acid (145 mg, 1.13 mmol), dichlorobis(triphenylphosphine)palladium(II) (26 mg, 0.037 mmol), 2 M sodium carbonate (335 mg in 1.6 mL water), and 1,2-dimethoxyethane (6 mL) in a manner analogous to the procedure described in Example 8.
Electrospray-MS 340.0 (M*+1). The compound of example 10 has been specifically excluded from the scope of the present invention.

EXAMPLE 11
Preparation of [(Methylethyl)sulfonyl]{2-[4-(4-(2-thienyl)phenyl)phenoxy]propyl}amine.

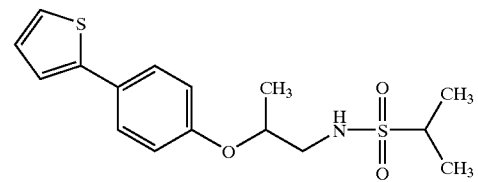

Scheme II, step E: The title compound (145 mg, 54%, yellow foam) was prepared from [2-(4-bromophenoxy)

propyl][(methylethyl)sulfonyl]amine (265 mg, 0.788 mmol, prepared in example 1), 2-thienylboronic acid (125 mg, 0.946 mmol), dichlorobis(triphenylphosphine)palladium(II) (22 mg, 0.031 mmol), 2 M sodium carbonate (285 mg in 1.35 mL water), and 1,2-dimethoxyethane (5.25 mL) in a manner analogous to the procedure described in Example 8.

Electrospray-MS 340.0 (M*+1).

EXAMPLE 12

Preparation of 4-[4-(1-Methyl-2-{[(methylethyl)sulfonyl]amino}ethoxy)phenyl]benzaldehyde.

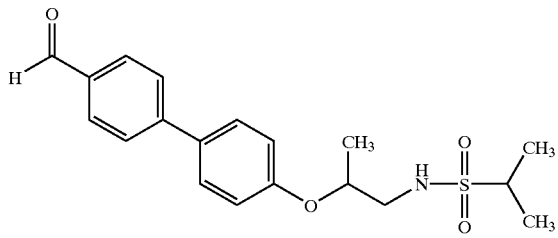

Scheme II, step E: The title compound (82 mg, 30%, yellow foam) was prepared from [2-(4-bromophenoxy)propyl][(methylethyl)sulfonyl]amine (252 mg, 0.749 mmol, prepared in example 1), 4-formylbenzeneboronic acid (135 mg, 0.900 mmol), dichlorobis(triphenylphosphine)palladium(II) (21 mg, 0.030 mmol), 2 M sodium carbonate (270 mg in 1.3 mL water), and 1,2-dimethoxyethane (5 mL) in a manner analogous to the procedure described in Example 8.

Electrospray-MS 362.0 (M*+1).

EXAMPLE 13

Preparation of [2-(4-(2H-Benzo[3,4-d]1,3-dioxolan-5-yl)phenoxy)propyl][(methylethyl)sulfonyl]amine.

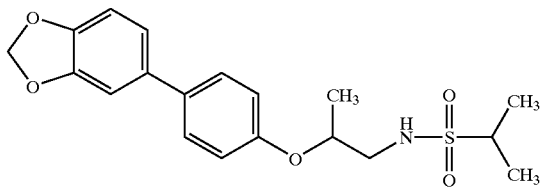

Scheme II, step E: The title compound (68 mg, 24%, white foam) was prepared from [2-(4-bromophenoxy)propyl][(methylethyl)sulfonyl]amine (250 mg, 0.7435 mmol, prepared in example 1), 3,4-methylenedioxybenzeneboronic acid (150 mg, 0.904 mmol), dichlorobis(triphenylphosphine)palladium(II) (21 mg, 0.030 mmol), 2 M sodium carbonate (270 mg in 1.3 mL water), and 1,2-dimethoxyethane (5 mL) in a manner analogous to the procedure described in Example 8. The crude material was purified utilizing a Chromatotron® with a 2000 μm rotor in a 1:1 hexane:ethyl acetate solvent system, yielding 140 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.

Electrospray-MS 378.0 (M*+1).

EXAMPLE 14

Preparation of [(Methylethyl)sulfonyl]{2-[4-(4-methylphenyl)phenoxy]propyl}amine.

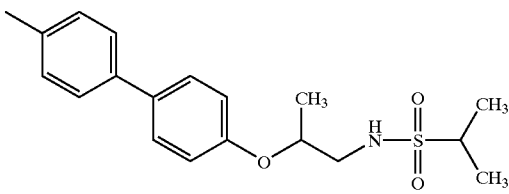

Scheme II, step E: The title compound (40 mg, 16%, white foam) was prepared from [2-(4-bromophenoxy)propyl][(methylethyl)sulfonyl]amine (239 mg, 0.711 mmol, prepared in example 1), 4-methylbenzeneboronic acid (116 mg, 0.853 mmol), dichlorobis(triphenylphosphine)palladium(II) (20 mg, 0.028 mmol), 2 M sodium carbonate (255 mg in 1.2 mL water), and 1,2-dimethoxyethane (4.75 mL) in a manner analogous to the procedure described in Example 8. The crude material was purified utilizing a Chromatotron® with a 2000 μm rotor in a 1:1 hexane:ethyl acetate solvent system, yielding 207 mg of a co-eluting mixture of unreacted starting material and title compound. This mixture was further purified is by reverse phase chromatography on a Vydac C-18 column on a gradient of 5 to 70% of 0.1% trifluoroacetic acid/acetonitrile in water over 45 minutes at 200 mL/min elution rate.

Electrospray-MS 348.0 (M*+1).

EXAMPLE 15

Preparation of 3-[4-(1-Methyl-2-{[(methylethyl)sulfonyl]amino}ethoxy)phenyl]benzaldehyde.

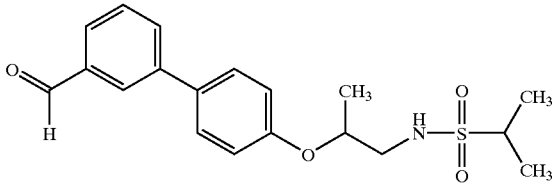

Scheme II, step E: The title compound (130 mg, 46%, yellow foam) was prepared from [2-(4-bromophenoxy)propyl][(methylethyl)sulfonyl]amine (265 mg, 0.788 mmol, prepared in example 1), 3-formylbenzeneboronic acid (160 mg, 0.964 mmol), dichlorobis(triphenylphosphine)palladium(II) (22 mg, 0.031 mmol), 2 M sodium carbonate (285 mg in 1.35 mL water), and 1,2-dimethoxyethane (5.25 mL) in a manner analogous to the procedure described in Example 8.

Electrospray-MS 362.0 (M*+1).

EXAMPLE 16

Preparation of [(Methylethyl)sulfonyl](2-{4-[3-(trifluoromethyl)phenyl]phenoxy}propyl)amine.

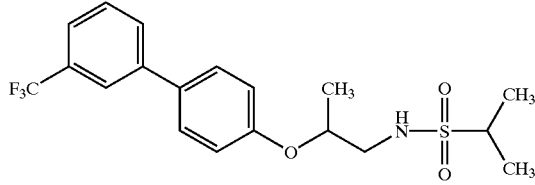

Scheme II, step E: The title compound (44 mg, 15%, white foam) was prepared from [2-(4-bromophenoxy)propyl][(methylethyl)sulfonyl]amine (240 mg, 0.714 mmol, prepared in example 1), 3-trifluoromethylbenzeneboronic acid (162 mg, 0.853 mmol), dichlorobis(triphenylphosphine)palladium(II) (20 mg, 0.028 mmol), 2 M sodium carbonate (255 mg in 1.2 mL water), and 1,2-dimethoxyethane (4.75 mL) in a manner analogous to the procedure described in Example 8. The crude material was purified utilizing a Chromatotron® with a 2000 μm rotor in a 1:1 hexane:ethyl acetate solvent system, yielding 192 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.
Electrospray-MS 402.0 (M*+1).

EXAMPLE 17
Preparation of 2-[4-(1-Methyl-2-{[(methylethyl)sulfonyl]amino}ethoxy)phenyl]benzaldehyde.

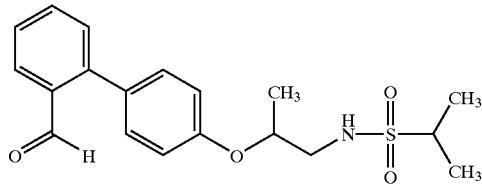

Scheme II, step E: The title compound (68 mg, 21%, white foam) was prepared from [2-(4-bromophenoxy)propyl][(methylethyl)sulfonyl]amine (300 mg, 0.892 mmol, prepared in example 1), 2-formylbenzeneboronic acid (180 mg, 1.085 mmol), dichlorobis(triphenylphosphine)palladium(II) (25 mg, 0.036 mmol), 2 M sodium carbonate (320 mg in 1.5 mL water), and 1,2-dimethoxyethane (6 mL) in a manner analogous to the procedure described in Example 8. The crude material was purified utilizing a Chromatotron® with a 2000 μm rotor in a 1:1 hexane:ethyl acetate solvent system, yielding 280 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.
Electrospray-MS 362.0 (M*+1).

EXAMPLE 18
Preparation of [(Methylethyl)sulfonyl](2-{4-[4-(trifluoromethyl)phenyl]phenoxy}propyl)amine.

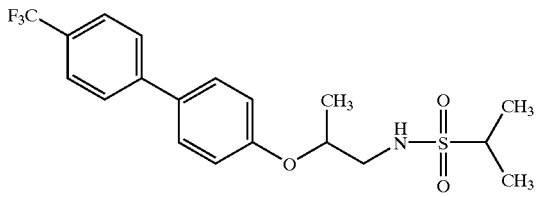

Scheme II, step E: The title compound (68 mg, 21.5%, white foam) was prepared from [2-(4-bromophenoxy)propyl][(methylethyl)sulfonyl]amine (267 mg, 0.794 mmol, prepared in example 1), 4-trifluoromethylbenzeneboronic acid (180 mg, 0.948 mmol), dichlorobis(triphenylphosphine)palladium(II) (22 mg, 0.031 mmol), 2 M sodium carbonate (285 mg in 1.35 mL water), and 1,2-dimethoxyethane (5.25 mL) in a manner analogous to the procedure described in Example 8. The crude material was purified utilizing a Chromatotron® with a 2000 μm rotor in a 1:1 hexane:ethyl acetate solvent system, yielding 190 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.
Electrospray-MS 402.0 (M*+1).

EXAMPLE 19
Preparation of {2-[4-(4-Methoxyphenyl)phenoxy]propyl}[(methylethyl)sulfonyl]amine.

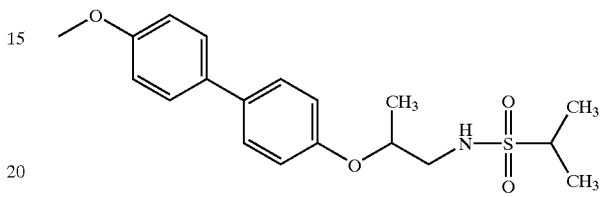

Scheme II, step E: The title compound (34 mg, 14%, white foam) was prepared from [2-(4-bromophenoxy)propyl][(methylethyl)sulfonyl]amine (225 mg, 0.669 mmol, prepared in example 1), 4-methoxybenzeneboronic acid (125 mg, 0.822 mmol), dichlorobis(triphenylphosphine)palladium(II) (20 mg, 0.028 mmol), 2 M sodium carbonate (245 mg in 1.15 mL water), and 1,2-dimethoxyethane (4.5 mL) in a manner analogous to the procedure described in Example 8. The crude material was purified utilizing a Chromatotron® with a 2000 μm rotor in a 1:1 hexane:ethyl acetate solvent system, yielding 220 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.
Electrospray-MS 364.0 (M*+1).

EXAMPLE 20
Preparation of {2-[4-(2-Fluorophenyl)phenoxy]propyl}[(methylethyl)sulfonyl]amine.

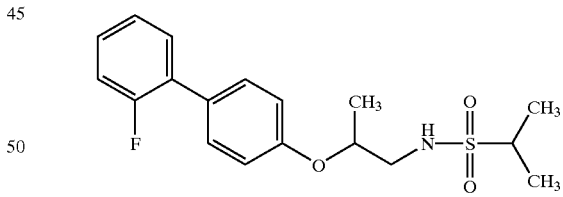

Scheme II, step E: The title compound (50 mg, 18%, white foam) was prepared from [2-(4-bromophenoxy)propyl][(methylethyl)sulfonyl]amine (260 mg, 0.773 mmol, prepared in example 1), 2-fluorobenzeneboronic acid (130 mg, 0.929 mmol), dichlorobis(triphenylphosphine)palladium(II) (22 mg, 0.031 mmol), 2 M sodium carbonate (280 mg in 1.3 mL water), and 1,2-dimethoxyethane (5.2 mL) in a manner analogous to the procedure described in Example 8. The crude material was purified utilizing a Chromatotron® with a 2000 μm rotor in a 1:1 hexane:ethyl acetate solvent system, yielding 230 mg of a co-eluting mixture of unreacted starting material and title compound. This mixture was further purified by reverse phase chromatography on a Vydac C-18 column on a gradient of 5 to 70%

EXAMPLE 21

Preparation of {2-[4-(4-Fluorophenyl)phenoxy]propyl}[(methylethyl)sulfonyl]amine.

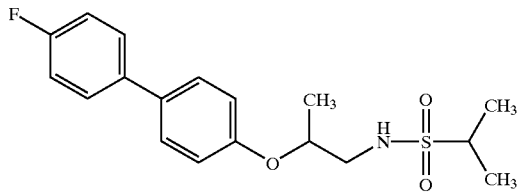

Scheme II, step E: The title compound (60 mg, 21%, white foam) was prepared from [2-(4-bromophenoxy)propyl][(methylethyl)sulfonyl]amine (275 mg, 0.818 mmol, prepared in example 1), 4-fluorobenzeneboronic acid (140 mg, 1.001 mmol), dichlorobis(triphenylphosphine)palladium(II) (23 mg, 0.033 mmol), 2 M sodium carbonate (295 mg in 1.4 mL water), and 1,2-dimethoxyethane (5.5 mL) in a manner analogous to the procedure described in Example 8. The crude material was purified utilizing a Chromatotron® with a 2000 µm rotor in a 1:1 hexane:ethyl acetate solvent system, yielding 310 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.

Electrospray-MS 352.0 (M*+1).

EXAMPLE 22

Preparation of {2-[4-(3-Methoxyphenyl)phenoxy]propyl}[(methylethyl)sulfonyl]amine.

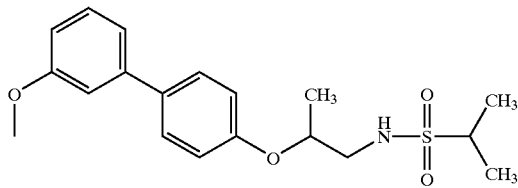

Scheme II, step E: The title compound (110 mg, 35%, white foam) was prepared from [2-(4-bromophenoxy)propyl][(methylethyl)sulfonyl]amine (290 mg, 0.862 mmol, prepared in example 1), 3-methoxybenzeneboronic acid (160 mg, 1.053 mmol), dichlorobis(triphenylphosphine)palladium(II) (25 mg, 0.036 mmol), 2 M sodium carbonate (310 mg in 1.5 mL water), and 1,2-dimethoxyethane (5.75 mL) in a manner analogous to the procedure described in Example 8. The crude material was purified utilizing a Chromatotron® with a 2000 µm rotor in a 1:1 hexane:ethyl acetate solvent system, yielding 350 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.

Electrospray-MS 364.0 (M*+1).

EXAMPLE 23

Preparation of {2-[4-(3-Fluorophenyl)phenoxy]propyl}[(methylethyl)sulfonyl]amine.

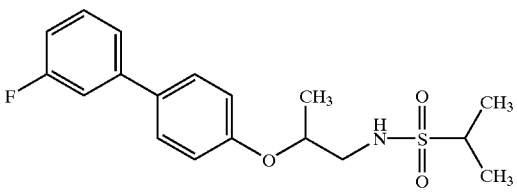

Scheme II, step E: The title compound (85 mg, 30%, white foam) was prepared from [2-(4-bromophenoxy)propyl][(methylethyl)sulfonyl]amine (275 mg, 0.818 mmol, prepared in example 1), 3-fluorobenzeneboronic acid (140 mg, 1.001 mmol), dichlorobis(triphenylphosphine)palladium(II) (23 mg, 0.033 mmol), 2 M sodium carbonate (295 mg in 1.4 mL water), and 1,2-dimethoxyethane (5.5 mL) in a manner analogous to the procedure described in Example 8. The crude material was purified utilizing a Chromatotron® with a 2000 µm rotor in a 1:1 hexane:ethyl acetate solvent system, yielding 270 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.

Electrospray-MS 352.0 (M*+1).

EXAMPLE 24

Preparation of [(Methylethyl)sulfonyl](2-{4-[2-(trifluoromethyl)phenyl]phenoxy}propyl)amine.

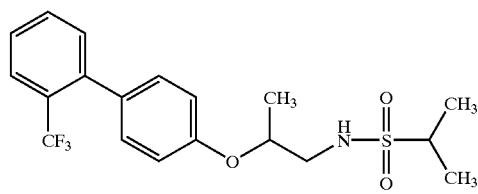

Scheme II, step E: The title compound (75 mg, 17%, white foam) was prepared from [2-(4-bromophenoxy)propyl][(methylethyl)sulfonyl]amine (375 mg, 1.115 mmol, prepared in example 1), 3-fluorobenzeneboronic acid (255 mg, 1.343 mmol), dichlorobis(triphenylphosphine)palladium(II) (32 mg, 0.046 mmol), 2 M sodium carbonate (400 mg in 1.9 mL water), and 1,2-dimethoxyethane (7.5 mL) in a manner analogous to the procedure described in Example 8. The crude material was purified utilizing a Chromatotron® with a 2000 µm rotor in a 1:1 hexane:ethyl acetate solvent system, yielding 270 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.

Electrospray-MS 402.0 (M*+1).

EXAMPLE 25

Preparation of {2-[4-(4-Cyanophenyl)phenoxy]propyl}[(methylethyl)sulfonyl]amine.

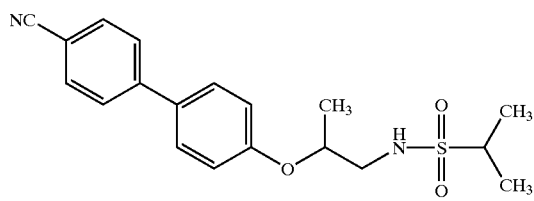

Preparation of 4-Cyanobenzeneboronic Acid.

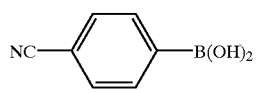

Following a modified literature procedure of Perria, G. J.; et al., *J. Am. Chem. Soc.*, 118, 10220–10227 (1996), a solution of 4-bromobenzonitrile (91 g, 0.50 mole) in THF (1.1 L) was dried in the presence of activated 3 Å molecular sieves at room temp. This solution was filtered and cooled to −100° C. Next, 1.6 M solution of n-butyllithium in hexanes (355 mL; 0.567 mol) was added to the cold solution over 15 min while maintaining the internal temperature between −105 and −93° C. To the resulting orange reaction mixture trimethylborate (81 g, 0.78 mol) was added over 3 min, briefly increasing the reaction temperature to −72° C. The reaction mixture was re-cooled to −100° C. over 5 min and then was allowed to warm slowly to room temperature over 2.3 h. The reaction mixture was acidified with 4N HCl to pH 2.2 and was diluted with $CH_2Cl_2$ (200 mL). The aqueous layer was separated and the organic layer was washed with brine (2×200 mL), dried ($MgSO_4$), filtered, and reduced under pressure to give a pale yellow solid. This solid was additionally purified by dissolution in 1N NaOH and extraction into $CH_2Cl_2$/THF (1:1, 2×200 mL). The aqueous phase was acidified with 4N HCl to pH 2.2 and was extracted into $CH_2Cl_2$/THF (1:1, 500 mL). The combined organic extracts were concentrated to a crude solid (64.6 g) that was triturated with diethyl ether (160 mL) and dried under vacuum to afford the intermediate title compound (44.0 g, 59.9%) as a white powder.

$^1$H NMR ($d_6$-acetone, 300 MHz): δ 8.03 (d, 2H, J=8.1), 7.75 (d, 2H, J=8.4), 7.54 (s, 2H).

Preparation of Final Title Compound.

Scheme II, step E: The final title compound (128 mg, 60%) was prepared from [2-(4-bromophenoxy)propyl][(methylethyl)sulfonyl]amine (200 mg, 0.595 mmol, prepared in example 1), 4-cyanobenzeneboronic acid (105 mg, 0.715 mmol), tetrakis(triphenylphosphine)palladium(0) (3.7 mg, 0.003 mmol), 2 M sodium carbonate (212 mg in 1 mL water) and 1,4-dioxane (4 mL) in a manner analogous to the procedure described in Example 2. It is understood that the final title compound name for example 25 above, {2-[4-(4-cyanophenyl)phenoxy]propyl}[(methylethyl)sulfonyl]amine, is equivalent to the alternative name of 4-[4-(1-methyl-2-{[(methylethyl)sulfonyl]amino}ethoxy)phenyl]benzenecarbonitrile.

Electrospray-MS 359.0 (M*+1).

Analysis

Theory: C 63.66, H 6.19, N 7.82.
Found: C 63.67, H 5.84, N 8.00.

EXAMPLE 25A

Preparation of 4-[4-((1R)-1-methyl-2-{[(methylethyl)sulfonyl]amino}ethoxy)phenyl]benzenecarbonitrile.

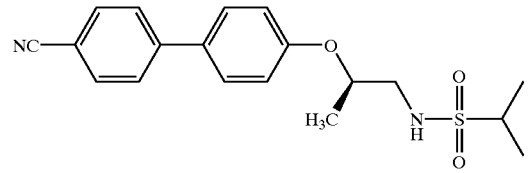

Preparation of (2R)-2-(4-bromophenoxy)propanamide:

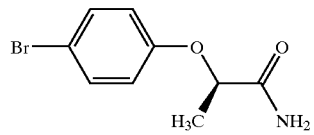

and preparation of (2S)-2-(4-bromophenoxy)propanamide.

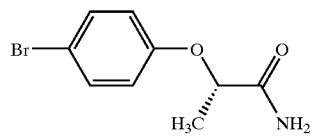

2-(4-Bromophenoxy)propanamide (prepared in example 1) is separated into the (2R)-2-(4-bromophenoxy)propanamide and (2S)-2-(4-bromophenoxy)propanamide enantiomers using standard techniques well known in the art. For example, 2-(4-bromophenoxy)propanamide can be separated into the corresponding enantiomers using chiral chromatography on a Chiralcel OD® column (Chiral Technologies, Inc., 730 Springdale Drive, Exton, Pa. 19341, 4.6×250 mm) with an eluent of 20% isopropanol/heptane at a flow rate of 1 mL/min.

Elemental Analysis for (2S)-2-(4-bromophenoxy)propanamide.
C(Theory): 44.2872 C(Found): 41.17
H(Theory): 4.1295 H(Found): 4.02
N(Theory): 5.7383 N(Found): 5.72

Elemental Analysis for (2R)-2-(4-bromophenoxy)propanamide.
C(Theory): 44.2872 C(Found): 44.51
H(Theory): 4.1295 H(Found): 4.21
N(Theory): 5.7383 N(Found): 5.60

Preparation of [(2R-2-(4-bromophenoxy)propyl][(methylethyl)sulfonyl]amine.

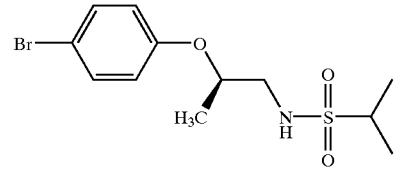

Scheme II, steps C and D: (2R)-2-(4-bromophenoxy)propanamide (4.0 g, 16.4 mmol), borane dimethylsulfide reagent (16.4 mL, 164 mmol), and THF (196 mL) were combined in a 2000 mL 3-neck round bottomed flask, affixed with a thermometer, condenser, and rubber stopper. Under a nitrogen atmosphere, with stirring, the reaction mixture was refluxed at 70° C. overnight. When the reaction was complete by TLC, it was cooled to ambient temperature. THF:methanol (49.2 mL, 1:1) was added by syringe, and when foaming ceased, 5N NaOH added by syringe. The reaction mixture was heated at 55° C. for an additional five hours, monitoring occasionally to determine if the borane complexes had been thoroughly broken up. Upon completion, the reaction mixture was cooled to room temperature, and extracted three times with methylene chloride. The organic layer was dried with sodium sulfate, filtered, and concentrated under reduced pressure, yielding 5.88 g of a viscous yellow oil. This oil was dissolved into 200 mL of diethyl ether, and acidified with concentrated HCl gas, to pH<2. The acidic solution was stirred at RT for one hour, then vacuum filtered off white precipitate. The precipitate was heated under vacuum for two hours at 40° C., yielding 2.85 g white solid. This solid was dissolved in methylene chloride 110 mL) in a 500 mL 3-neck round bottomed flask, fitted with a thermometer, rubber stopper, and under a nitrogen system. The reaction mixture was then cooled to 0° C., triethylamine (5.7 mL, 41.0 mmol) and isopropylsulfonyl chloride (2.76 mL, 24.6 mmol) respectively, were added by syringe and stirred overnight monitored until complete. The reaction was monitored by TLC until complete. The reaction was then quenched with 200 mL water, and the layers were separated. The organic layer was washed with water, dried with sodium sulfate, filtered, and concentrated under reduced pressure yielding 4.16 g viscous brown oil. The product was further purified by chromatography on a waters Prep 2000 using two Prep-Paks, in a 50:50 is hexanes:ethyl acetate solvent system. This yielded the intermediate title compound (2.81 g, 51%) as a slow crystallizing viscous brown oil.

Preparation of final title compound, 4-[4-((1R)-1-methyl-2-{[(methylethyl)sulfonyl]amino}ethoxy)phenyl]benzenecarbonitrile.

Scheme II, step E: 4-Cyanobenzeneboronic acid (171 mg, 1.16 mmol, prepared in example 25), tetrakis(triphenylphosphine)palladium(0) (69 mg, 0.063 mmol), 2 M sodium carbonate (1.6 mL), and [(2R)-2-(4-bromophenoxy)propyl][(methylethyl)sulfonyl]amine (310 mg, 0.922 mmol) were combined in a 15 mL round bottomed flask with dimethylethylene glycol (6.15 mL, DME), fitted with a condenser, stirbar, and in a temperature regulated oil bath, and refluxed in a nitrogen system to 85° C., overnight. The reaction was allowed to cool to room temperature, and quenched with 15 mL of water, and extracted three times with 15 mL ethyl acetate. The organic layer was dried with magnesium sulfate, filtered through Celite®, and concentrated under reduced pressure, yielding 470 mg viscous black oil. This material was further purified using a 4000 uM rotor on a Chromatotron® in a 1:1 hexanes:ethyl acetate solvent system yielding the final title compound (57.5 mg, 18%) as white crystals.

MS-ES M*+1 (359.5).
Elemental Analysis:
C(Theory): 63.66 C(Found): 62.81
H(Theory): 6.19 H(Found): 5.99
N(Theory): 7.81 N(Found): 7.73

EXAMPLE 25B

Preparation of 4-[4-((1S)-1-methyl-2-{[(methylethyl)sulfonyl]amino}ethoxy)phenyl]benzenecarbonitrile.

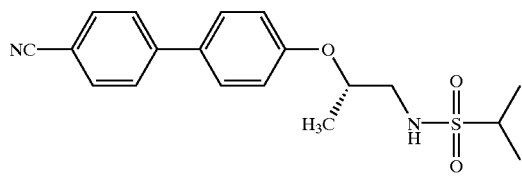

The title compound is prepared in a manner analogous to the procedure set forth in example 25A from (2S)-2-(4-bromophenoxy)propanamide (prepared in exampel 25A).

EXAMPLE 26

Preparation of 2-{4-[4-(1-Methyl-2-{[(methylethyl)sulfonyl]amino}ethoxy)phenyl]phenyl}ethanenitrile.

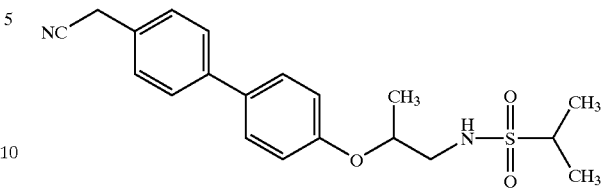

Preparation of 4-(cyanomethyl-phenylboronic acid, pinacol ester.

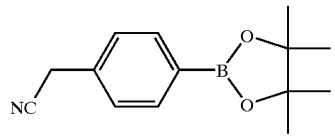

Using the method of Murata, M., et al., Y. J. Org. Chem, 62 6458–6459 (1997), 4-iodophenylacetonitrile (23.9 g, 0.100 mol), Et₃N (42 mL, 0.30 mol), acetonitrile (400 mL) and Pd(dppf)₂Cl₂ catalyst ([1,1'-bis(diphenylphosphino)ferrocene]dichloropalladium(II) complex with CH₂Cl₂) were combined in a 1 L flask and the resulting solution was evacuated and purged with nitrogen three times. The pinacolborane (22 mL, 0.15 mol) was added and the mixture was heated at reflux for 3 h. ¹H NMR analysis of an aliquot indicated complete consumption of starting 4-iodophenylacetonitrile. The mixture was cooled to room temperature, concentrated to an oil and taken up in CH₂Cl₂. This solution was extracted with 0.1 N HCl (3×100 mL) and the organic phase was separated, concentrated and re-dissolved in methyl tert-butyl ether (MTBE). The MTBE solution was passed through a filter packed with silica gel (300 g). The eluant was concentrated to a dark red oil. This oil was extracted with hexanes (500 mL) and the soluble fraction was decanted away from a black oil (5 g). MTBE (5 mL) was added to this oil to give a suspension that was filtered through Celite®. This filtrated was combined with the hexanes fraction and the solution was concentrated to an oil. Finally, the oil was re-dissolved in di-isopropyl ether (150 mL) and was diluted with hexanes (400 mL). This mixture was allowed to stand for 2 h, and then filtered to remove a dark precipitate. The resulting amber filtrate was concentrated to an oil, re-dissolved in hexanes (400 mL) and concentrated to 75 mL without added heat. This treatment resulted in the precipitation of the desired intermediate title compound as a golden waxy solid that was air-dried to afford 23.0 g (96.2%):

¹H NMR (CDCl₃, 300 MHz): δ 7.8 (d, 2H); 7.35 (d, 2H); 3.8 (s, 2H) 1.15 (s, 12H).

Preparation of 4-(cyanomethyl)-phenylboronic acid.

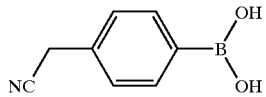

Using the method of Coutts, S. J., et al., Tetrahedron Lett., 35, 5109–5112 (1994), 4-(cyanomethyl)-phenylboronic acid, pinacol ester (25.0 g, 0.103 mol) was dissolved in acetone (500 mL) and water (27 mL). To this solution, 1N aqueous ammonium acetate was added (256 mL), followed by NaIO$_4$ (66.9 g, 0.300 mol). The turbid mixture was stirred under nitrogen for 2 h at room temperature to afford a thicker suspension. The reaction mixture was filtered and the filter cake was washed with acetone (3×30 mL) and water (1×50 mL). The filtrated was concentrated to a solid that was suspended in water (30 mL) and filtered. The filtrate was discarded. The combined collected solids were slurried in acetone (200 mL) and filtered. The filtrate was concentrated and the residue was dissolved in acetone (100 mL). A small amount of acetone-insoluble material was removed by filtration. The combined filtrates were concentrated to provide the intermediate title compound (18.9 g, 114%).
$^1$H NMR (d$_6$-acetone, 300 MHz) revealed the presence of H$_2$O in this lot: δ 7.90 (d, 2H, J=8.1), 7.38 (d, 2H, J=8.1), 7.25 (br, s, 2H), 3.97 (s, 2H).
Preparation of Final Title Compound.

Scheme II, step E: The final title compound (80 mg, 48%) was prepared from [2-(4-bromophenoxy)propyl] [(methylethyl)sulfonyl]amine (150 mg, 0.446 mmol, prepared in example 1), 4-(cyanomethyl)-phenylboronic acid (197 mg, 1.502 mmol), tetrakis(triphenylphosphine) palladium(0) (3.0 mg, 0.003 mmol), 2 M sodium carbonate (212 mg in 1 mL water) and 1,4-dioxane (4 mL) in a manner analogous to the procedure described in Example 2.
Electrospray-MS 373.0 (M*+1).
Analysis
Theory: C 64.49, H 6.49, N 7.52.
Found: C 64.65, H 6.08, N 7.56.

EXAMPLE 27

Preparation of [(Methylethyl)sulfonyl][2-(4-{3-[(methylsulfonyl)amino]phenyl}phenoxy)propyl]amine.

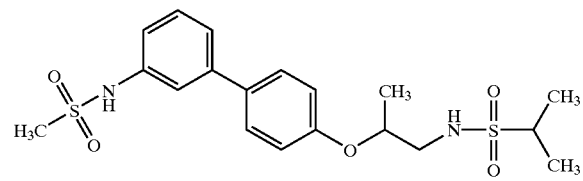

Preparation of benzotriazolyl methylsulfonate.

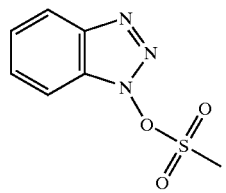

The intermediate title compound was prepared following a procedure adapted from Tet. Lett., 40 (1), 117 (1999). To a slurry of hydroxybenztriazole hydrate (10.0 g, 74.0 mmoles) in methylene chloride (100 mL) was added triethylamine (15.0 g, 148 mmoles) followed by a methylene chloride rinse (4–5 mL). The solution was cooled to 4° C. and a solution of methanesulfonyl chloride (8.48 g, 74.0 mmoles) in methylene chloride (25 mL) was added dropwise with stirring. HPLC analysis revealed 78.9% hydroxybenztriazole and 21.1% benzotriazolyl methylsulfonate (relative area percent). An additional portion of triethylamine (7.0 g, 69.2 mmoles) was introduced to the reaction vessel, followed by additional solution of methanesulfonyl chloride (8.48 g, 74.0 mmoles) in methylene chloride (25 mL) added dropwise at 8° C. HPLC analysis revealed 9% hydroxybenztriazole and 85% benzotriazolyl methylsulfonate (relative area percent).

The reaction mixture was allowed to warm to room temperature and then was suction filtered through a silica gel plug (20 g) capped with Celite. The solid filtration media was rinsed with fresh methylene chloride (2×100 mL). The filtrate was concentrated to a yellow paste (38.8 g) under reduced pressure. The crude paste was partitioned between MTBE (200 mL) and water (150 mL) to form a clear, two phase mixture. The organic phase was separated and extracted with water (2×150 mL). The organic phase was dried (Na$_2$SO$_4$), filtered, and the filtrate was concentrated, under vacuum, to afford 12.2 g of a yellow oil that spontaneously solidified to a yellow solid.

Recrystallization of this solid was accomplished by dissolution in warm MTBE (50 mL), followed by the slow addition of heptanes (50 mL), stirring and slow cooling to room temperature. The mixture was stirred for an additional 15–20 min and was suction filtered at room temperature and the solid was rinsed with heptanes (5×). The solids were suction dried to afford 9.04 g (57.3%) of benzotriazolyl methylsulfonate as a white solid. The filtrate was refiltered and the 2$^{nd}$ crop was rinsed 2× with heptane. The additional solids were collected to obtain 0.46 g of additional white solid of benzotriazolyl methylsulfonate for a total yield of (9.5 g, 62.5%). $^1$H NMR (300 MHz, CDCl$_3$) δ 8.1 (d, 1H), 7.4–7.7 (m, 3H), 3.6 (s, 3H).
Preparation of 3-(amino)-phenylboronic acid, pinacol ester

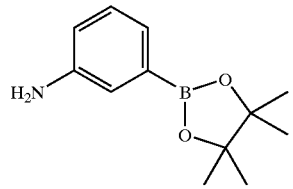

3-Aminophenylboronic acid hydrate 97% (4.48 g, 0.029 mol) and pinacol (3.42 g, 0.030 mol) in methylene chloride (50 mL) were stirred for 17 h. HPLC analysis at 17 h revealed some unreacted boronic acid. After 2 days of stirring at room temperature the reaction was shown to be complete (HPLC). The reaction mixture was extracted with 10% K$_2$CO$_3$ (2×50 mL) and the organic phase was separated and dried (Na$_2$SO$_4$). After filtration, the organic phase was concentrated under reduced pressure to afford 4.41 g (71.7%) of 3-(amino)-phenylboronic acid, pinacol ester as tan powder. $^1$H NMR (CDCl$_3$, 300 MHz): δ 7.10–7.24 (3H, m), 6.79 (1H, ddd, J=1.8, 2.7, 7.2), 3.62 (2H, brs), 1.34 (12H, s).
Preparation of 3-[(methylsulfonyl)amino]phenylboronic acid, pinacol ester.

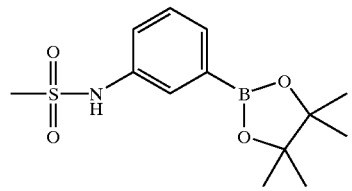

A solution of 3-(amino)-phenylboronic acid, pinacol ester (5.00 g, 22.8 mmoles) and benzotriazolyl methyl (5.35 g, 25.1 mmoles) in DMF (50 mL) was heated to 50° C. with stirring under nitrogen. The reaction was followed by HPLC. Complete conversion of aniline to sulfonamide was observed after 44 h of reaction. The mixture was allowed to cool and was diluted with MTBE (250 mL) and water (100 mL). The heterogeneous mixture was shaken well and allowed to separate. The organic phase was isolated and extracted with water (2×100 mL), 10% K$_2$CO$_3$ (1×100 mL) and again with water (1×100 mL). The organic phase was isolated, dried (Na$_2$SO$_4$), filtered, and concentrated to afford 0.78 g of a mixture of mono and bis sulfonamides as a brown oil.

The desired 3-[(methylsulfonyl)amino]phenylboronic acid, pinacol ester was recovered from the alkaline aqueous layer, by cooling the 10% K$_2$CO$_3$ washings (0° C.) and acidifying with the dropwise addition of concentrated sulfuric acid with stirring until a white precipitate was observed. The mixture was stirred cold for an additional 0.5 h and then suction filtered, the solids rinsed with water (3×) and air-dried overnight to afford 1.06 g (16%) of pure 3-[(methylsulfonyl)amino]phenylboronic acid, pinacol ester as a white solid.

Alternative preparation of 3-[(methylsulfonyl)amino] phenylboronic acid, pinacol ester.

3-(amino)-Phenylboronic acid, pinacol ester (54.6 g, 249 mmoles) was dissolved in methylene chloride (250 mL) and treated with activated 3A sieves (26 g). This mixture was gravity filtered into a 2L round bottom flask and rinsed in with additional methylene chloride (250 mL). Triethylamine (50.4 g, 498 mmoles) was added to the reaction vessel with stirring at room temperature followed by a methylene chloride rinse (100 mL). The reaction mixture was is cooled to 1–2° C. with stirring under nitrogen and a solution of methanesulfonyl chloride (28.3 g, 247 mmoles)in methylene chloride (100 mL) was added dropwise over 40 min, followed by a methylene chloride rinse (25 mL). The mixture exothermed to 5° C. throughout the addition. After 30 min of stirring the reaction was allowed to warm to room temperature. After 6 days of stirring at room temperature. 1 N HCl (250 mL) was added dropwise with stirring at room temperature. After stirring for 30 min, the organic phase was isolated, dried (Na$_2$SO$_4$), and silica gel (100 g) was added to the mixture with swirling. The mixture was suction filtered through a silica plug (800 g) capped with celite and the fitration medium was rinsed through with the following rinses:

1. methylene chloride (4×200 mL): clear, colorless filtrate.
2. EtOAc (3×1000 mL): pale yellow filtrate.
3. EtOAc (1×1000 mL): clear, colorless filtrate.

The above filtration lots were concentrated under reduced pressure.

| Filtrate Lot | Solvent | Concentrate |
| --- | --- | --- |
| 1 | CH$_2$Cl$_2$ | 0.2 grams |
| 2 | EtOAc | 73.3 grams |
| 3 | EtOAc | 0.12 grams |

Lot 2 concentrate (73.3 g) was diluted with EtOAc (210 mL) and was seeded with authentic 3-[(methylsulfonyl)amino] phenylboronic acid, pinacol ester. Heptane (630 mL) was then added dropwise to the product solution at room temperature with stirring. Precipitation had occurred. The mixture was cooled to 1–2° C. for 1.5 h then suction filtered. The collected solids were rinsed with heptane (2×200 mL). The solids were air-dried under suction for 20 min to afford 50.0 g (68.2%) of 3-[(methylsulfonyl)amino]phenylboronic acid, pinacol ester as a white solid. $^1$NMR (DMSO-d$_6$, δ 9.7 (s, 1H), 7.5–7.3 (m, 4H), 2.95 (s, 3H), 1.24 (s, 12H); H$_2$O: 3.3(s).

Scheme II, step E: The final title compound (30 mg, 10%) was prepared from [2-(4-bromophenoxy)propyl] [(methylethyl)sulfonyl]amine (260 mg, 0.773 mmol, prepared in example 1), 3-[(methylsulfonyl)amino] phenylboronic acid, pinacol ester (276 mg, 0.929 mmol, prepared above), tetrakis(triphenylphosphine)palladium(0) (5 mg, 0.004 mmol), 2 M sodium carbonate (280 mg in 1.3 mL water) and 1,4-dioxane (5.2 mL) in a manner analogous to the procedure described in Example 2.
Electrospray-MS 425.1 (M*–1).

EXAMPLE 28

Preparation of Ethyl 4-[4-(1-methyl-2-{[(methylethyl) sulfonyl]amino}ethoxy)phenyl]benzoate.

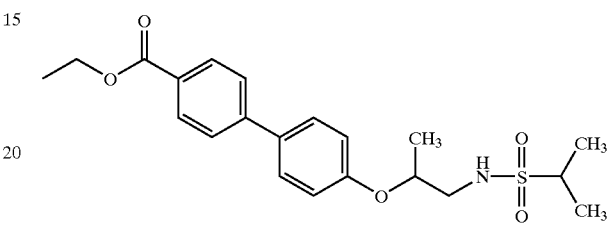

Preparation of 4-(ethoxycarbonyl)benzeneboronic acid.

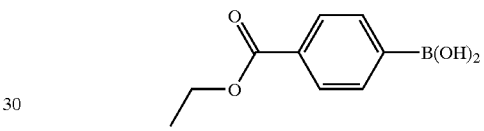

4-Carboxybenzeneboronic acid (350 mg, 2.109 mmol) was dissolved in ethanol (10 mL, absolute) in a 100 mL 3-neck round bottom flask, fitted with a condenser, thermometer, stirbar and rubber plug. An ethanol/HCl mixture (10 mL, pH approximately 3.0) was added, and the mixture was heated at reflux (70° C.) for one hour. The reaction mixture was then allowed to cool to room temperature and stirred overnight. The reaction mixture was concentrated in a vacuum, then dissolved in ethyl acetate, and washed with water. The organic layer was dried with potassium carbonate, filtered, and concentrated under reduced pressure, yielding 520 mg white solid. This material was purified via silica gel chromatography, utilizing a Chromatotron® with a 6000 μm rotor in a 1:1 hexane:ethyl acetate solvent system, yielding 470 mg of a co-eluting mixture of unreacted starting material and product. This mixture was purified by reverse phase chromatography on a Vydac C-18 column on a gradient of 5 to 70% of 0.1% trifluoroacetic acid/acetonitrile in water yielding the intermediate title compound (350 mg, 85.5%) as a white solid.
Electrospray-MS 195.0 (M*+1).
Preparation of Final Title Compound.

Scheme II, step E: The title compound (6 mg, 1%, white foam) was prepared from [2-(4-bromophenoxy)propyl] [(methylethyl)sulfonyl]amine (505 mg, 1.502 mmol, prepared in example 1), 4-(ethoxycarbonyl)benzeneboronic acid (350 mg, 1.804 mmol), dichlorobis (triphenylphosphine)palladium(II) (45 mg, 0.064 mmol), 2 M sodium carbonate (540 mg in 2.6 mL water), and 1,2-dimethoxyethane (10 mL) in a manner analogous to the procedure described in Example 8. The crude material was purified utilizing a Chromatotron® with a 2000 μm rotor in a 1:1 hexane:ethyl acetate solvent system, yielding 20 mg of a co-eluting mixture of unreacted starting material and title compound. This mixture was further purified by reverse phase chromatography on a Vydac C-18 column on a gradient of 5 to 70% of 0.1% trifluoroacetic acid/acetonitrile in water over 45 minutes at 200 mL/min elution rate.
Electrospray-MS 406.0 (M*+1).

EXAMPLE 29
Preparation of N-{4-[4-(1-Methyl-2-{[(methylethyl)sulfonyl]amino}ethoxy)phenyl]phenyl}acetamide.

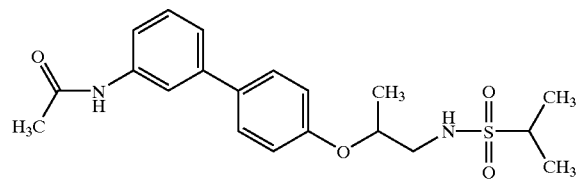

Scheme III, step C: To a solution of {2-[4-(3-Aminophenyl)phenoxy]propyl}[(methylethyl)sulfonyl]amine (125 mg, 0.3587 mmol, prepared in example 3) in methylene chloride (2.5 mL) in a 10 mL round-bottomed flask, in an ice bath, fitted with a thermometer, and under a nitrogen system was added triethylamine (0.125 mL, 0.8968 mmol). The mixture was cooled to 0° C. and acetyl chloride 0.04 mL, 0.5381 mmol) was added by syringe. The mixture was allowed to warm to room temperature, and stirred overnight, under a nitrogen system. The reaction was quenched with excess water, and the organic layer was dried with anhydrous sodium sulfate, filtered, and concentrated under reduced vacuum, yielding 265 mg viscous oil. Purification was conducted using a Chromatotron®, on a 4000 μm rotor and eluting with a 1:1 hexane:ethyl acetate solvent system, yielding the title compound (104 mg, 74%) as a slow crystallizing foam.
Electrospray-MS 391.0 (M*+1).

EXAMPLE 30
Preparation of 2-Methyl-N-{4-[4-(1-methyl-2-{[(methylethyl)sulfonyl]amino}ethoxy)phenyl]phenyl}propanamide.

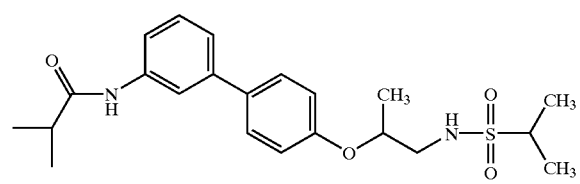

Scheme III, step C: To a solution of {2-[4-(3-aminophenyl)phenoxy]propyl}[(methylethyl)sulfonyl]amine (145 mg, 0.416 mmol, prepared in example 3) dissolved in methylene chloride (2.8 mL, anhydrous), was added triethylamine (0.15 mL, 1.04 mmol) under a nitrogen system. The mixture was cooled to 0° C. and isobutyryl chloride (0.13 mL, 1.25 mmol) was added by syringe. The mixture was allowed to warm to room temperature, and stirred overnight, under a nitrogen system. The reaction was quenched with excess water, and the organic layer was dried with anhydrous sodium sulfate, filtered, and concentrated under reduced vacuum, yielding 280 mg viscous oil. Purification was conducted using a Chromatotron®, on a 4000 μm rotor and eluting with a 1:1 hexane:ethyl acetate solvent system, yielding the title compound (136 mg, 78%) as a slow crystallizing foam.
Electrospray-MS 419.0 (M*+1).

EXAMPLE 31
Preparation of [(Methylethyl)sulfonyl]{2-[4-(3-{[(methylethyl)sulfonyl]amino}phenyl)phenoxy]propyl}amine.

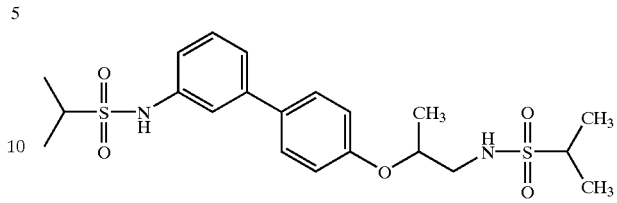

Scheme III, step B: To a solution of {2-[4-(3-aminophenyl)phenoxy]propyl}[(methylethyl)sulfonyl]amine (125 mg, 0.3587 mmol, prepared in example 3) dissolved in methylene chloride (2.5 mL, anhydrous) was added triethylamine (0.125 mL, 0.8968 mmol) under a nitrogen system. The mixture was cooled to 0° C. and 2-propanesulfonyl chloride (0.06 mL, 0.5381 mmol) was added by syringe. The mixture was allowed to warm to room temperature, and stirred overnight, under a nitrogen system. The reaction was quenched with excess water, and the organic layer was dried with anhydrous sodium sulfate, filtered, and concentrated under reduced pressure, yielding 431 mg viscous oil. Purification was conducted using a Chromatotron®, on a 4000 μm rotor and eluting with a 1:1 hexane:ethyl acetate solvent system, yielding 400 mg of two inseparable coeluting spots. This mixture was purified by reverse phase chromatography on a Vydac C-18 column on a gradient of 5 to 70% of 0.1% trifluoroacetic acid/acetonitrile in water over 45 minutes at 200 mL/min elution rate, yielding the title compound (16.7 mg, 1%) as a slow crystallizing foam.
Electrospray-MS 455.0 (M*+1).

EXAMPLE 32
Preparation of (2-{4-[4-(Aminomethyl)phenyl]phenoxy}propyl)[(methylethyl)sulfonyl]amine hydrochloride.

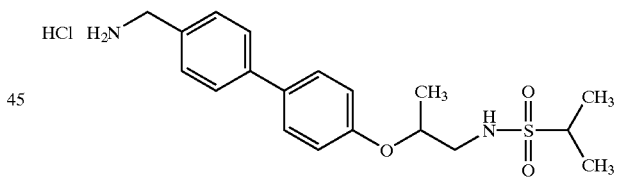

Scheme III, step A: In a 100 mL 3-neck flask, fitted with a thermometer, a stirbar and a condenser, {2-[4-(4-cyanophenyl)phenoxy]propyl}[(methylethyl)sulfonyl]amine (1.0 g, 2.79 mmol, prepared in example 25), borane-methyl sulfide complex (13.95 mL, 27.9 mmol), and tetrahydrofuran (33.5 mL) were combined and heated at reflux, with stirring, at 70° C., overnight, under a nitrogen system. The reaction mixture was allowed to cool to room temperature, and 8.5 mL of 1:1 tetrahydrofuran:methyl alcohol mixture was added dropwise, slowly, until foaming ceased. Next, 5N sodium hydroxide was added, and the reaction mixture was refluxed for 5 hours. The mixture was then permitted to cool to room temperature and extracted three times with 50 mL of methylene chloride. The organic layer was dried with potassium carbonate, filtered, and concentrated under reduced vacuum, yielding 2.47 g of viscous purple oil. This oil was dissolved into diethyl ether, and acidified with anhydrous hydrogen choride gas. The acid mixture was allowed to stir at room temperature for 1 hour, forming a white precipitate. The precipitate was captured by vacuum filtration yielding the title compound (1.34 g, 100%) as an off-white solid.
Electrospray-MS 363.0 (M*+1).

EXAMPLE 33
Preparation of [(Methylethyl)sulfonyl]({4-[4-(1-methyl-2-{[(methylethyl)sulfonyl]amino}ethoxy)phenyl]phenyl}methyl)amine.

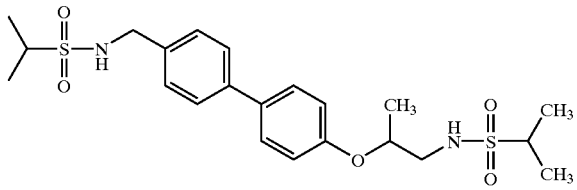

Scheme III, step B: The final title compound (140 mg, 69.5%) was prepared from (2-{4-[4-aminomethyl)phenyl]phenoxy}propyl)[(methylethyl)sulfonyl]amine hydrochloride (150 mg, 0.430 mmol, prepared in example 32) methylene chloride (2.5 mL, anhydrous), triethylamine (0.07 mL, 0.471 mmol) and 2-propanesulfonyl chloride (0.07 mL, 0.565 mmol) in a manner analogous to Example 29.
Electrospray-MS 469.0 (M*+1).

EXAMPLE 34
Preparation of [(Methylethyl)sulfonyl](2-{4-[4-({[(trifluoromethyl)sulfonyl]amino}methyl)phenyl]phenoxy}propyl)amine.

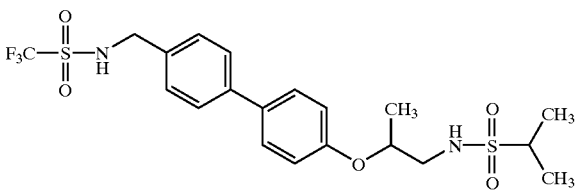

Scheme III, step B: The final title compound (23 mg, 11%) was prepared from (2-{4-[4-(aminomethyl)phenyl]phenoxy}propyl)[(methylethyl)sulfonyl]amine hydrochloride (150 mg, 0.430 mmol, prepared in example 32) methylene chloride 2.5 mL, anhydrous) triethylamine (0.07 mL, 0.471 mmol) and trifluoromethylsulfonyl chloride (9.06 mL, 0.565 mmol), in a manner analogous to Example 29.
Electrospray-MS 495.0 (M*+1).

EXAMPLE 35
Preparation of 2-Methyl-N-({4-[4-(1-methyl-2-{[(methylethyl)sulfonyl]amino}ethoxy)phenyl]phenyl}methyl)propanamide.

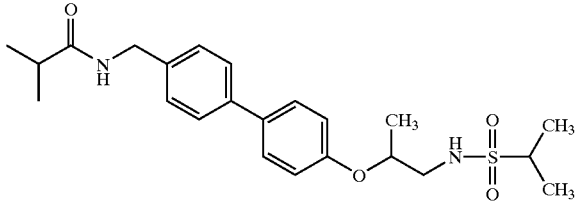

Scheme III, step C: The final title compound (59 mg, 19%) was prepared from (2-{4-[4-(aminomethyl)phenyl]

phenoxy}propyl)[(methylethyl)sulfonyl]amine hydrochloride (250 mg, 0.717 mmol, prepared in example 32) methylene chloride (4.6 mL, absolute) triethylamine (0.07 mL, 0.8621 mmol), aind isobutyryl chloride (0.06 mL, 1.0345 mmol), in a manner analogous to Example 29.
Electrospray-MS 433.0 (M*+1).

EXAMPLE 36
Preparation of [(Methylethyl)sulfonyl]{2-[4-(4-{[(methylsulfonyl)amino]methyl}phenyl)phenoxy]propyl}amine.

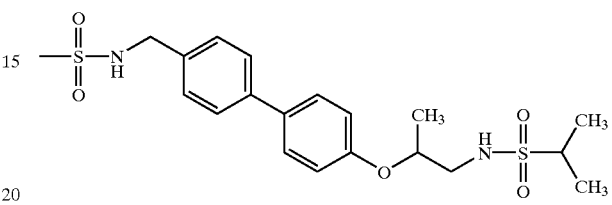

Scheme III, step B: The final title compound (10 mg, 3%) was prepared from (2-{4-[4-(aminomethyl)phenyl]phenoxy}propyl)[methylethyl)sulfonyl]amine hydrochloride (250 mg, 0.717 mmol, prepared in example 32) methylene chloride (4.6 mL, anhydrous) triethylamine (0.12 mL, 0.8621 mmol) and methanesulfonyl chloride (0.08 mL, 1.0345 mmol), in a manner analogous to Example 29.
Electrospray-MS 441.0 (M*+1).

EXAMPLE 37
Preparation of N-({4-[4-(1-Methyl-2-{[(methylethyl)sulfonyl]amino}ethoxy)phenyl]phenyl}methyl)acetamide.

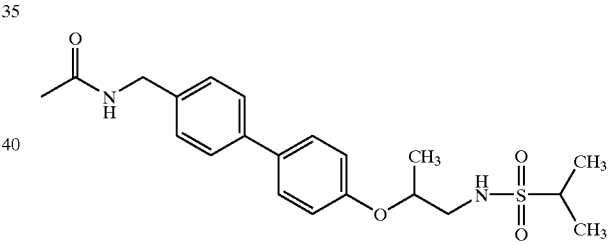

Scheme III, step C: The final title compound (98 mg, 42%) was prepared from (2-{4-[4-(aminomethyl)phenyl]phenoxy}propyl)[(methylethyl)sulfonyl]amine hydrochloride (200 mg, 0.5739 mmol, prepared in example 32) methylene chloride (3.8 mL, anhydrous) triethylamine (0.12 mL, 0.6620 mmol) and acetyl chloride (0.08 mL, 0.6069 mmol), in a manner analogous to Example 29.
Electrospray-MS 405.0 (M*+1).

EXAMPLE 38
Preparation of (tert-butoxy)-N-(2-{4-[4-(1-methyl-2-{[(methylethyl)sulfonyl]amino}ethoxy)phenyl]phenyl}ethyl)carboxamide.

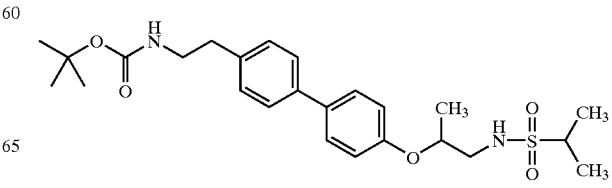

Preparation of 2,2,2-trifluoro-N-(2-phenylethyl) acetamide.

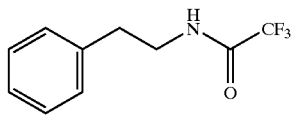

To a solution of phenethylamine (242 g, 2.0 moles) in dichloromethane (1.2 L) was added triethylamine (213 g, 2.1 moles) and was cooled to −5° C. Trifluoroacetic anhydride (441 g, 2.1 moles) was added to the reaction mixture dropwise over 10 min. During the addition the reaction mixture exothermed to 22° C. This mixture was stirred at room temperature for 30 min. Acetic acid (5 mL) was added and the mixture was extracted with water (3×50 mL). The organic phase was co-evaporated with hexanes to afford 431 g (99.3%) of intermediate title compound, 2,2,2-trifluoro-N-(2-phenylethyl)acetamide, as a solid mass that was carried directly into the following reaction.

Preparation of 2,2,2-trifluoro-N-[2-(4-iodophenyl)ethyl] acetamide.

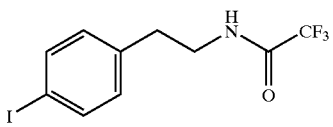

To a room temperature solution of 2,2,2-trifluoro-N-(2-phenylethyl)acetamide (431 g, 1.98 moles) in glacial acetic acid (1.5 L) was added water (400 mL), sulfuric acid (200 g, 2.04 moles), periodic acid (105 g, 0.46 mol), and lastly iodine (201 g, 0.791 mol). The mixture was first heated to 55° C., and then heated to 70° C. over 2 h. This temperature course avoided excessive exotherm during the starting phase of the reaction. After 3 h, GC analysis indicated 10% starting material remained. Another portion of iodine (7 g, 0.027 mol) and periodic acid (3.5 g, 0.015 mol) was introduced to the reaction mixture. Sublimed iodine that deposited on the upper region of the reactor was washed into the reaction with a minimum of acetic acid. The reaction mixture was further heated at 70° C. for 30 min and was allowed to stand at room temperature overnight.

Sodium acetate (351 g, 4.08 moles) was added to neutralize the sulfuric acid, followed by the addition of sodium sulfite until the mixture decolorized. The mixture was cooled to 10° C. and was filtered. The filter cake was washed with 1:1 acetic acid-water (400 mL), water (500 mL) and was reslurried in 1:9 acetic acid-water (1 L). After a final water wash and reslurry with water (1 L), the collected solids were filtered and vacuum dried at 45° C. This procedure afforded 354 g (52.1%) of intermediate title compound, 2,2,2-trifluoro-N-[2-(4-iodophenyl)ethyl]acetamide, as a white powder.

$^1$H NMR (CDCl$_3$, 300 MHz): δ 7.66 (d, 2H, J=8.4); 6.94 (d, 2H, J=8.4); 6.31 (br s, 1 H); 3.59 (q, 2H, J=6.9); 2.84 (t, 2H, J=6.9).

Preparation of pinacolborane.

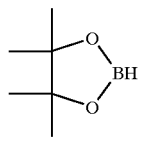

A 5 L round bottom flask was charged with pinacol (177 g, 1.5 moles) and CH$_2$Cl$_2$ (1.6 L). The borane-dimethylsulfide (10 M,159 mL, 0.16 mol) was added to the flask via cannula and the mixture was stirred at 0° C. for 4 h. The reaction mixture was then allowed to warm to room temperature overnight with stirring.

After 17 h, the reaction mixture was still evolving some gas (hydrogen);

however, the reaction was warmed and subjected slowly to reduced pressure (760 mm to 200 mm). This procedure allowed the distillation of CH$_2$Cl$_2$ (1.3 L) from the reaction. The remaining liquid was transferred by cannula to a 500 mL flask and was subjected to a slow pressure reduction from atmospheric to 50 mm over 2.5 h. Some initial foaming was observed in the viscous liquid due to continued off-gassing that subsided in time. This process afforded 157 g (81.7%) of crude pinacolborane that was suitable for the subsequent reactions.

Preparation of 2,2,2-trifluoro-N-[2-(4-boronic acid)phenyl) ethyl]acetamide, pinacol ester.

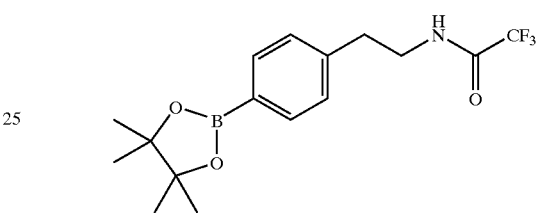

In a manner analogous to the procedure described by Murata, M., et al., J. Org. Chem, 62, 6458–64592 (1997), 2,2-trifluoro-N-[2-(4-iodophenyl)ethyl]acetamide (313 g, 0.912 mol), Et$_3$N (277 g, 2.73 moles), acetonitrile (2.5L) and Pd(dppf)$_2$Cl$_2$ catalyst were combined in a 5 L reactor and the resulting solution was evacuated and purged with nitrogen three times. The pinacolborane (146 g, 1.14 moles) generated above was added and the mixture was heated to 70° C. for 3.5 h. GC analysis of an aliquot indicated extensive consumption of starting 2,2,2-trifluoro-N-[2-(4-iodophenyl) ethyl]acetamide (0.4%) along with the generation of intermediate title compound (76.9%). The mixture was cooled to room temperature, concentrated to an oil and redissolved in heptane. The heptane was decanted away from an insoluble black residue and concentrated to 210 g of a yellow oil. The heptane insoluble tar was diluted with heptane (500 mL) and water (500 mL). This mixture was warmed to 70° C. and separated. The heptane phase was concentrated to an oil. The heptane-extracted products were combined and purified via Biotage chromatography (2.5 Kg silica gel, presaturated with CH$_2$Cl$_2$). Fractions containing 96–98.5% intermediate title compound (by GC) were combined and concentrated to a solid that was triturated with cyclohexane (100 mL), filtered and dried under reduced pressure to afford 120 g of intermediate title compound. Mixed fractions containing intermediate title compound and 20–52% 2,2,2-trifluoro-N-(2-phenylethyl)acetamide (byproduct obtained by reductive removal of the iodine atom) were combined, concentrated, crystallized with cyclohexane. This crop was triturated with cyclohexane to afford additional intermediate title compound (9 g). This treatment resulted in the total isolation of 129 g (31.9%) of desired intermediate title compound, 2,2,2-trifluoro-N-[2-(4-(boronic acid)phenyl)ethyl] acetamide, pinacol ester, as a white solid: $^1$H NMR (CDCl$_3$, 300 MHz): δ 7.78 (d, 2H, J=7.8); 7.20 (d, 2H, J=7.5); 6.21 (br s, 1H); 3.62 (q, 2H, J=6.6); 2.90 (t, 2H, J=6.6); 1.32 (s, 12H).

Preparation of tert-butyl {2,2,2-trifluoro-N-[2-(4-(boronic acid)phenyl)ethyl]acetylamino}formate, pinacol ester.

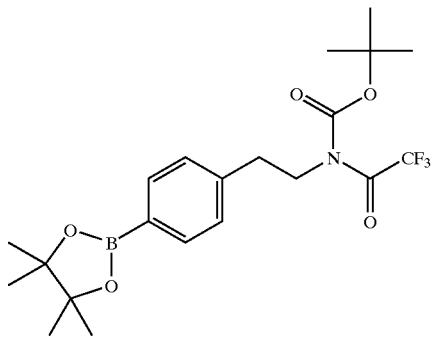

To a solution of 2,2,2-trifluoro-N-[2-(4-boronicacid)phenyl)ethyl]acetamide, pinacol ester (100 g, 0.291 mol) in CH₂Cl₂ (1.0 L) was added 4-N,N dimethylaminopyridine (1.78 g, 0.0146 mol), followed by di-tert-butyl dicarbonate (70.0 g, 0.320 mol). The resulting mixture was allowed to stir at room temperature overnight. After 17 h, the reaction mixture was washed with deionized water (2×300 mL). The organic phase was concentrated to a solid that was dried under vacuum to afford 128.9 g (99.8%) intermediate title compounde as a white powder.
(CDCl₃, 300 MHz): δ 7.75 (d, 2H, J=4.8); 7.22 (d, 2H, J=4.5); 3.92 (t, 2H, J=4.8); 2.91 (t, 2H, J=4.5); 1.48 (s, 9H); 1.33 (s, 12H).

Preparation of 4-{2-[(tert-butoxy)carbonylamino]ethyl}boronic acid, pinacol ester.

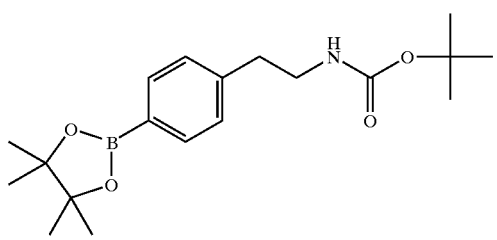

To a stirred solution of of tert-butyl {2,2,2-trifluoro-N-[2-(4-(boronic acid)phenyl)ethyl]acetylamino}formate, pinacol ester (125 g, 0.282 mol) in n-propanol (750 mL) and diethyl ether (150 mL) was added a solution of sodium carbonate (44.8 g, 0.423 mol) in water (500 mL). After 2 h, HPLC analysis indicated nearly complete hydrolysis of the trifluoroacetamide group. The aqueous phase was separated and the organic phase was concentrated to a thick white paste. This paste was suspended in pentane and filtered. The filtrate was similarly concentrated, resuspended in pentane/diethyl ether (1:1) and filtered to afford white solids. The crops were combined and dried under reduced pressure to give 106 g (108%) of intermediate title compound, 4-{2-[(tert-butoxy)carbonylamino]ethyl}boronic acid, pinacol ester as a white powder. (CDCl₃, 300 MHz): δ 7.67 (d, 2H, J=4.8); 7.24 (d, 2H, J=4.5); 6.01 (br s, 1H); 3.30 (q, 2H, J=4.2); 2.81 (t, 2H, J=4.2); 1.39 (s, 9H); 1.32 (s, 12H).

Preparation of Final Title Compound.

Scheme II, step E: [2-(4-Bromophenoxy)propyl][(methylethyl)sulfonyl]amine (1.875 g, 5.576 mmol, prepared in example 1), 4-{2-[(tert-butoxy)carbonylamino]ethyl}boronic acid, pinacol ester, (2.26 g, 6.508 mmol), dichlorobis(triphenylphosphine)palladium(II) (155 mg, 0.221 mmol), 2M sodium carbonate (1.96 g in 9.25 mL water) and 1,2-dimethoxyethane (36 mL) were combined in a 100 mL 3-neck round bottom flask, fitted with a condenser, stirbar, and thermometer, and heat at reflux in a nitrogen system to 85° C. overnight. The room temperature reaction mixture was quenched with water and extracted three times with 25 mL of methylene chloride. The organic extracts were combined, dried over anyhydrous magnesium sulfate, filtered through celite, and concentrated under reduced pressure, yielding 4.0 g brown viscous oil. This material was purified via silica gel chromatography, utilizing a Hewlett-Packard HPLC 2000 with 2 silica cartridges in a 1:1 hexane:ethyl acetate solvent system, yielding the final title compound (610 mg, 29%), (tert-butoxy)-N-(2-{4-[4-(1-methyl-2-{[(methylethyl)sulfonyl]amino}ethoxy)phenyl]phenyl}ethyl)carboxamide, as a white solid.
Electrospray-MS 477.0 (M*+1).

EXAMPLE 39

Preparation of (2-{4-[4-(2-Aminoethyl)phenyl]phenoxy}propyl)[(methylethyl)sulfonyl]amine hydrochloride.

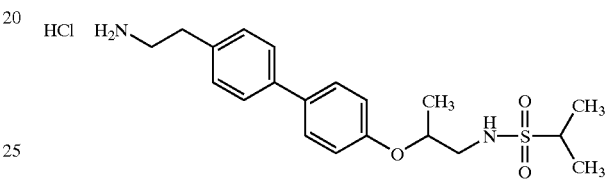

(tert-Butoxy)-N-(2-{4-[4-(1-methyl-2-{[(methylethyl)sulfonyl]amino}ethoxy)phenyl]phenyl}ethyl)carboxamide (410 mg, 0.860 mmol, prepared in example 38), trifluoroacetic acid (0.86 mL), and methylene chloride (5.75 mL) were combined and stirred, by stirbar, in a 15 mL round bottom flask, in a nitrogen system, at room temperature, for one hour. The reaction mixture was then concentrated under reduced pressure, and dissolved in excess 5N sodium hydroxide, and extracted three times with 25 mL of methylene chloride. Next the organic extracts were combined, washed with 50 mL of water, dried with potassium carbonate, filtered, and concentrated under reduced vacuum, yielding 480 mg of crude material. This crude material was dissolved in diethyl ether, and anhydrous hydrogen chloride gas was bubbled through the solution, until it was acidic. Next, the acidic solution was allowed to stir, by stirbar, for an additional hour, and then was vacuum filtered, capturing the white precipitate and drying it in a vacuum oven at 40° C. for 30 minutes, yielding the title compound (305 mg, 94%) as a yellow solid.
Electrospray-MS 377.0 (M*+1).

EXAMPLE 40

Preparation of [(Methylethyl)sulfonyl](2-{4-[4-(2-{[(methylethyl)sulfonyl]amino}ethyl)phenyl]phenoxy}propyl)amine.

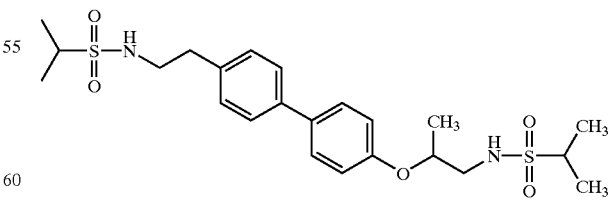

Scheme II, step B: To a 10 mL round-bottomed flask, in an ice bath, fitted with a thermometer, and under a nitrogen atmosphere, of (2-{4-[4-(2-aminoethyl)phenyl]phenoxy}propyl)[(methylethyl)sulfonyl]amine hydrochloride (150 mg, 0.3984 mmol, prepared in example 39) dissolved in methylene chloride (2.7 mL) was added triethylamine (0.07 mL, 0.478 mmol). Once the mixture was cooled to 0° C., 2-propanesulfonyl chloride (0.05 mL, 0.4382 mmol) was added by syringe, and the mixture was gradually warmed to room temperature, with stirring overnight. The reaction was quenched with excess water, and the organic layer was dried with anhydrous sodium sulfate, filtered, and concentrated under vacuum, yielding 265 mg viscous oil. Purification was conducted using a Chromatotron®, on a 4000 μm rotor and eluting with a 1:1 hexane:ethyl acetate solvent system, yielding the title compound (200 mg, 100%) as a slow crystallizing foam. Electrospray-MS 483.0 (M*+1).

EXAMPLE 41

Preparation of N-(2-{4-[4-(1-Methyl-2-{[(methylethyl)sulfonyl]amino}ethoxy)phenyl]phenyl}ethyl)acetamide.

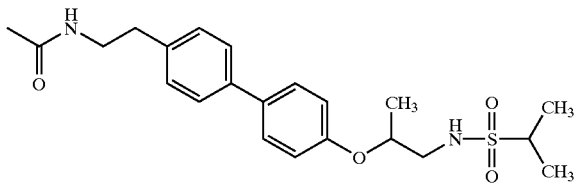

Scheme III, step C: The title compound (108 mg, 39%, slow crystallizing foam) was prepared from (2-{4-[4-(2-aminoethyl)phenyl]phenoxy}propyl)[(methylethyl)sulfonyl]amine hydrochloride (250 mg, 0.664 mmol, prepared in example 39), methylene chloride (4.5 mL, anhydrous), triethylamine (0.09 mL, 0.664 mmol), and acetyl chloride (0.05 mL, 0.664 mmol) in a manner analogous to the procedure described in Example 40. Electrospray-MS 419.0 (M*+1).

EXAMPLE 42

Prepation of 2-Methyl-N-(2-{4-[4-(1-methyl-2-{[(methylethyl)sulfonyl]amino}ethoxy)phenyl]phenyl}ethyl)propanamide.

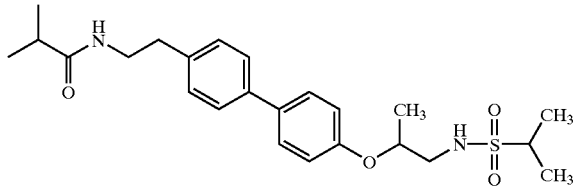

Scheme III, step C: The title compound (110 mg, 37%, slow crystallizing-foam) was prepared from (2-{4-[4-(2-aminoethyl)phenyl]phenoxy}propyl)[(methylethyl)sulfonyl]amine hydrochloride (250 mg, 0.664 mmol, prepared in example 39), methylene chloride (4.5 mL, anhydrous), triethylamine (0.09 mL, 0.664 mmol), and isobutyryl chloride (0.07 mL, 0.664 mmol) in a manner analogous to the procedure described in Example 40. Electrospray-MS 447.0 (M*+1).

EXAMPLE 43

Preparation of [(Methylethyl)sulfonyl]{2-[4-(4-{2-[(methylsulfonyl)amino]ethyl}phenyl)phenoxy]propyl}amine.

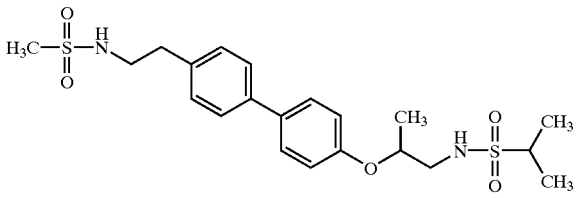

Scheme III, step B: The title compound (318 mg, 100%, slow crystallizing foam) was prepared from (2-{4-[4-(2-aminoethyl)phenyl]phenoxy}propyl)[(methylethyl)sulfonyl]amine hydrochloride (250 mg, 0.664 mmol, prepared in example 39), methylene chloride (4.5 mL, anhydrous), triethylamine (0.09 mL, 0.664 mmol), and methanesulfonyl chloride (0.05 mL, 0.664 mmol) in a manner analogous to the procedure described in Example 40. Electrospray-MS 455.0 (M*+1).

EXAMPLE 44

Preparation of [(Methylethyl)sulfonyl](2-{4-[4-(2-{[(trifluoromethyl)sulfonyl]amino}ethyl)phenyl]phenoxy}propyl)amine.

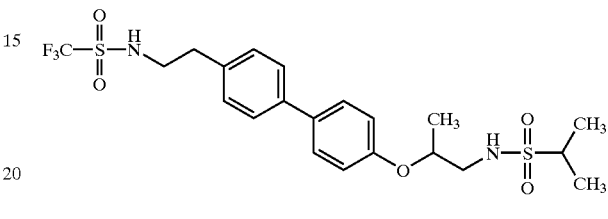

Scheme III, step B: The title compound (130 mg, 38%, slow crystallizing-foam) was prepared from (2-{4-[4-(2-aminoethyl)phenyl]phenoxy}propyl)[(methylethyl)sulfonyl]amine hydrochloride (250 mg, 0.664 mmol, prepared in example 39), methylene chloride (4.5 mL, anhydrous), triethylamine (0.09 mL, 0.664 mmol), and trifluoromethanesulfonyl chloride (0.07 mL, 0.664 mmol) in a manner analogous to the procedure described in Example 40.

EXAMPLE 45

Preparation of [(methylethyl)sulfonyl](2-{4-[4-(1-methyl-2-{[(methylethyl)sulfonyl]amino}ethoxy)phenyl]phenoxy}propyl)amine.

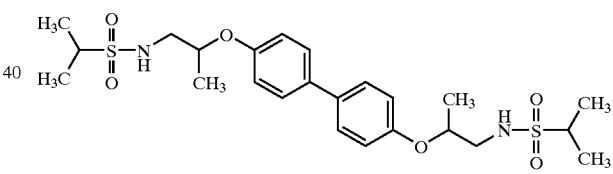

[2-(4-Bromophenoxy)propyl][(methylethyl)sulfonyl]amine (200 mg, 0.595 mmol), cyclopentylboronic acid (60 mg, 0.714 mmol), ([1,1'-bis(diphenylphosphino)ferrocene]dichloropalladium(II) complex with $CH_2Cl_2$ (4 mg, 0.024 mmol), and 2M sodium hydroxide (1 mL) were combined with THF (4 mL) in a 15 ml round-bottomed flask, fitted with a condenser, and stirbar, in a temperature regulated oil bath, and refluxed at 65° C. overnight in a nitrogen system. After cooling to room temperature, the reaction mixture was quenched with 15 mL of water, and extracted three times with 15 mL ethyl acetate. The organic extractions were combined and dried with magnesium sulfate, then filtered through Celite®, and concentrated in-vacuo, yielding 210 mg viscous black oil. This material was further purified using a 4000 uM rotor on a Chromatotron in a 1:1 hexanes-:ethyl acetate solvent system to provide the title compound (50 mg, 16%) as white crystals.
Electrospray-MS (511.4; singlet) M*−1
Elemental Analysis:
C(Theory): 56.23 C(Found): 55.92
H(Theory): 7.08 H(Found): 6.98
N(Theory): 5.46 N(Found): 5.60

EXAMPLE 46
Preparation of N-acetyl-N-{3-[4-(1-methyl-2-{[(methylethyl)sulfonyl]amino}ethoxy)phenyl]phenyl}acetamide.

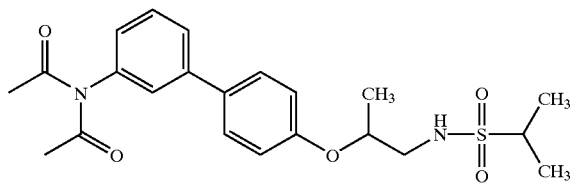

{2-[4-(3-Aminophenyl)phenoxy]propyl}[(methylethyl)sulfonyl]amine (150 mg, 0.3764 mmol, see example 3), triethylamine 0.125 mL, 0.8968 mmol), and methylene chloride 2.5 mL) were combined in a 15 mL round-bottomed, flask, fitted with stirbar, and cooled to 0° C. in an ice bath, in a nitrogen system. Acetyl chloride (0.04 mL, 0.5381 mmol) was added by syringe maintaining a temperature of 0–5° C. The reaction was allowed to stir overnight, gradually becoming room temperature. The reaction mixture was quenched with 15 mL of water, and extracted three times with 15 mL methylene chloride. The organic extractions were combined, and dried with magnesium sulfate, filtered, and concentrated in-vacuo, yielding 265 mg brown foam. This material was further purified by using a 4000 uM rotor on a Chromatotron, in a 1:1 hexanes:ethyl acetate solvent system to provide the title compound (74 mg, 48%) as white crystals.
Electrospray-MS (434.0; singlet) M*+1

EXAMPLE 47
Preparation of Methyl 4-[4-(1-methyl-2-{[(methylethyl)sulfonyl]amino}ethoxy)phenyl]benzoate.

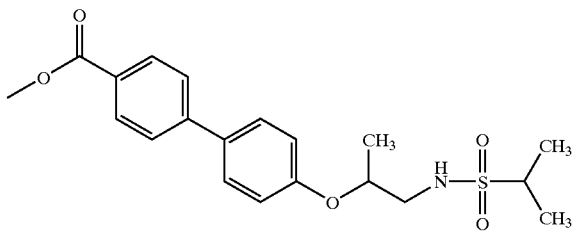

[2-(4-Bromophenoxy)propyl][(methylethyl)sulfonyl]amine (500 mg, 1.487 mmol) was combined with bis(pinicolato)diboron (415 mg, 1.636 mmol), potassium acetate (440 mg, 4.461 mmol), [1,1'-bis(diphenylphosphino)ferrocene]palladium(II) chloride complex (0.045 mmol) and dimethylformamide (10 mL) in a 3-neck round bottomed flask fitted with a thermometer, stirbar, condenser, and in a nitrogen system. This reaction mixture was refluxed to 80° C. with stirring, for three hours. The reaction mixture was cooled to room temperature, and [1,1'-bis(diphenylphosphino)ferrocene]palladium(II) chloride complex (0.045 mmol) was added, followed by 2M sodium carbonate (3.7 mL), and refluxed to 80° C., with stirring, overnight. The reaction was cooled to room temperature, and diluted with 100 mL of diethyl ether, and washed with 100 mL water and 100 mL brine. Organic layer was dried with potassium carbonate, filtered and concentrated in-vacuo, yielding 1.53 g of brown solid. This material was further purified using a 6000 uM rotor on a Chromatotron in a 1:1 hexanes:ethyl acetate solvent system to provide the title compound (50 mg, 9%) as yellow crystals.

Electrospray-MS (393.0; singlet) M*+1
Elemental Analysis:
C(Theory): 61.36 C(Found): 60.32
H(Theory): 6.44 H(Found): 6.27
N(Theory): 3.56 N(Found): 3.56

EXAMPLE 48
Preparation of 4-[4-(1-methyl-2-{[(methylethyl)sulfonyl]amino}ethoxy)phenyl]benzoic acid.

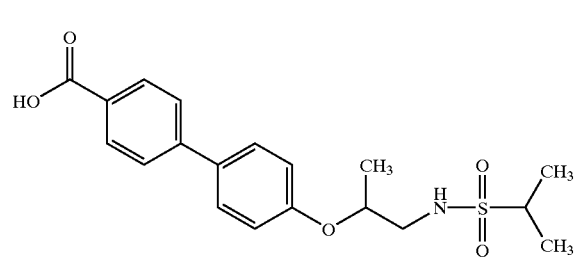

Methyl 4-[4-(1-methyl-2-{[(methylethyl)sulfonyl]amino}ethoxy)phenyl]benzoate (30 mg, 0.077 mmol), lithium hydroxide (11 mg, 0.268 mmol), THF (1.2 mL), methanol (0.4 mL) and deionized water (0.4 mL) were combined in a 15 mL round bottomed flask and stirred at room temperature overnight. The reaction mixture was concentrated in-vacuo, and dissolved in 1 N sodium hydroxide. This solution was acidified (pH=2) with 1 N hydrochloric acid, and was extracted three times with methylene chloride. The organic extractions were combined, washed with 15 mL water, dried with magnesium sulfate, filtered, and concentrated in-vacuo, yielding 85 mg of yellow solid. This material was further purified using a 1000 uM rotor on a Chromatotron in a 1:1 methylene chloride:ethyl acetate solvent system to provide the title compound (65 mg, 100%) as waxy brown paste.
Electrospray-MS (393.0; singlet) M*+1

EXAMPLE 49
Preparation of [(2S)-2-(4-bromophenoxy)propyl][(methylethyl)sulfonyl]amine.

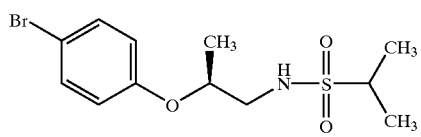

Preparation of (2S)-2-(4-bromophenoxy)propylamine hydrochloride.

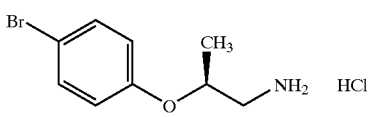

Scheme II, step C: (2S)-2-(4-bromophenoxy)propanamide (4.0 g, 16.39 mmol, see example 1A), borane dimethyl sulfide complex (16.4 mL, 163.9 mmol)), and tetrahydrofuran (50 mL) were combined in a 2000 mL 3-neck round bottomed flask, fitted with a thermometer, reflux condenser, and addition funnel. Under a nitrogen system the reaction mixture was refluxed at 70° C. overnight with stirring. The reaction mixture was cooled, and 1:1 tetrahydrofuran:methanol (50 mL) was added slowly. Once foaming had ceased, 5 N sodium hydroxide (150 mL) was added, and the reaction mixture was refluxed at 55° C., with stirring, for 5 hours. Next the reaction mixture was cooled to room temperature, and extracted three times with 400 mL methylene chloride. The organic extractions were combined and dried with sodium sulfate, filtered and concentrated in-vacuo, yielding 3.73 g yellow oil.

This material was dissolved in excess diethyl ether, and anhydrous hydrogen chloride gas was bubbled through the solution with stirring, until white crystals had precipitated out (pH=2). The solution was stirred for an additional hour, before the precipitate was vacuum filtered off, and washed two times with 100 mL of diethyl ether. This precipitate was dried in a vacuum oven for 2 hours at 40° C. yielding the intermediate title compound, (2S)2-(4-bromophenoxy) propylamine HCl, (1.48 g) as a white powder.
Preparation of Final Title Compound.

Scheme II, step D: The above prepared (2S)-2-(4-bromophenoxy)propylamine was combined in a 500 mL 3-neck round bottomed flask with triethylamine (5.7 mL) and methylene chloride (110 mL), fitted with a thermometer, stirbar, and in a nitrogen system. The reaction mixture was cooled to 0° C. in an ice bath, with stirring, and isopropyl-sulfonyl chloride (2.75 mL, 24.585 mmol) was added by syringe. The mixture was stirred overnight, gradually becoming room temperature. The reaction was quenched with 100 mL water, and extracted two times with 100 mL methylene chloride. The organic extractions were combined, and washed with 200 mL brine, dried with sodium sulfate, filtered and concentrated in-vacuo, yielding 2.08 g viscous brown oil. This material was further purified using one Waters Prep-Pak® on a Waters Prep 2000 HPLC, in a 3:1 hexanes:ethyl acetate solvent system to provide the final title compound (1.63 g, 30%) as a viscous yellow oil.
Electrospray-MS (336.0, 338.0; doublet) M*+1
Elemental Analysis:
C(Theory): 42.87 C(Found): 42.34
H(Theory): 5.40 H(Found): 5.05
N(Theory): 4.17 N(Found): 4.33

EXAMPLE 50
Preparation of [(2S)-2-(4-{3-[(methylsulfonyl)amino]phenyl}phenoxy)propyl][(methylethyl)sulfonyl]amine.

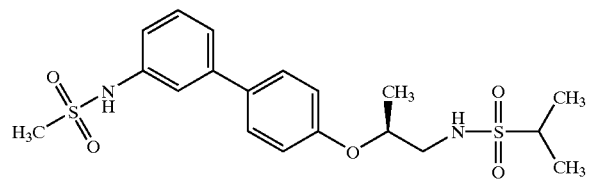

Scheme II, step E: [(2S)-2-(4-Bromophenoxy)propyl][(methylethyl)sulfonyl]amine (1.61 g, 4.788 mmol, see example 1A), 3-[(methylsulfonyl)amino]phenylboronic acid, pinacol ester (1.80 g, 6.033 mmol, example 27), tetrakis(triphenylphosphine)palladium(0) (360 mg, 0.3112 mmol), 2M sodium carbonate (8.15 mL) and dimethylene glycol (32 mL) were combined into a 100 mL round-bottomed flask, fitted with a condenser, and stirbar, in a temperature regulated oil bath, and refluxed at 85° C. overnight in a nitrogen system. After cooling to room temperature, the reaction mixture was quenched with 50 mL of water, and extracted three times with 50 mL ethyl acetate. The organic extractions were combined and dried with magnesium sulfate, then filtered through Celite®, and concentrated in-vacuo, yielding 2.76 g viscous black oil. This material was further purified using one Waters Prep-Pak® on a Waters Prep 2000 HPLC, in a 3:1 hexanes:ethyl acetate solvent system to provide the title compound (640 mg, 31%) as viscous yellow oil.
Electrospray-MS (427.0; singlet) M*–1
Elemental Analysis:
C(Theory): 53.50 C(Found): 52.91
H(Theory): 6.14 H(Found): 6.08
N(Theory): 6.57 N(Found): 6.47

EXAMPLE 51
Preparation of [(2R)-2-(4-{3-[(methylsulfonyl)amino]phenyl}phenoxy)propyl][(methylethyl)sulfonyl]amine.

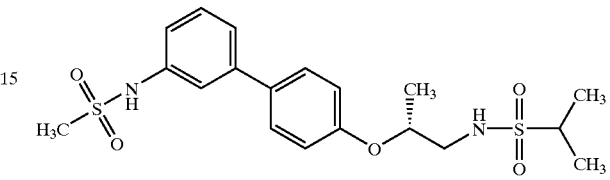

Scheme II, step E: [(2R)-2-(4-Bromophenoxy)propyl][(methylethyl)sulfonyl]amine (1.01 g, 3.004 mmol, see example 1B), 3-[(methylsulfonyl)amino]phenylboronic acid, pinacol ester (1.125 g, 3.785 mmol, example 27), tetrakis(triphenylphosphine)palladium(0) (226 mg, 0.1953 mmol), 2M sodium carbonate (5.1 mL) and dimethylene glycol (20 mL) were combined into a 100 mL round-bottomed flask, fitted with a condenser, and stirbar, in a temperature regulated oil bath, and refluxed at 85° C. overnight in a nitrogen system. After cooling to room temperature, the reaction mixture was quenched with 50 mL of water, and extracted three times with 50 mL ethyl acetate. The organic extractions were combined and dried with magnesium sulfate, then filtered through Celite®, and concentrated in-vacuo, yielding 1.07 g viscous black oil. This material was further purified using one Waters Prep-Pak® on a Waters Prep 2000 HPLC, in a 3:1 hexanes:ethyl acetate solvent system to provide the title compound (340 mg (0.80, 27%) as viscous yellow oil.
Electrospray-MS (427.0; singlet) M*–1
Elemental Analysis:
C(Theory): 53.50 C(Found): 53.31
H(Theory): 6.14 H(Found): 6.14
N(Theory): 6.57 N(Found): 6.41

EXAMPLE 52
Preparation of 4-[4-((1S)-1-methyl-2-{[(methylethyl)sulfonyl]amino}ethoxy)phenyl]benzenecarbonitrile.

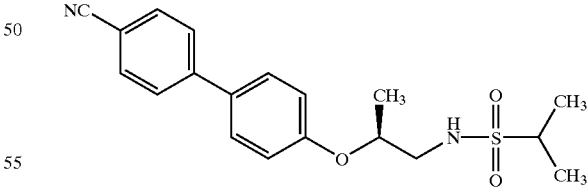

Scheme II, step E: [(2S)-2-(4-Bromophenoxy)propyl][(methylethyl)sulfonyl]amine (325 mg, 0.9665 mmol, see example 1A), 4-cyanoboronic acid (179 mg, 1.218 mmol), tetrakis(triphenylphosphine)palladium(0) (73 mg, 0.063 mmol), 2M sodium carbonate (1.65 mL) and dimethylene glycol (6.45 mL) were combined into a 50 mL round-bottomed flask, fitted with a condenser, and stirbar, in a temperature regulated oil bath, and refluxed at 85° C. overnight in a nitrogen system. After cooling to room temperature, the reaction mixture was quenched with 25 mL of water, and extracted three times with 25 mL ethyl acetate. The organic extractions were combined and dried with magnesium sulfate, then filtered through Celite®, and concentrated in-vacuo, yielding 590 mg viscous black oil. This material was further purified using a 4000 uM rotor on a Chromatotron in 1:1 hexanes:ethyl acetate solvent system to provide the title compound (130.5 mg, 38%) as viscous yellow oil.

Electrospray-MS (359.0; singlet) M*−1

Elemental Analysis:

C(Theory): 63.66 C(Found): 63.11

H(Theory): 6.19 H(Found): 6.02

N(Theory): 7.81 N(Found): 7.78

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK 293 cells stably expressing human GluR4B (obtained as described in European Patent Application Publication Number EP-A1-583917) are prepared. The tissue culture medium in the wells is then discarded, and the wells are each washed once with 200 μl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 μM Fluo3-AM dye (obtained from Molecular Probes Inc., Eugene, Oreg.) in buffer in each well. After the incubation, each well is washed once with 100 μl buffer, 200 μl of buffer is added and the plates are incubated for 30 minutes.

Solutions for use in the test are also prepared as follows. 30 μM, 10 μM, 3 μM and 1 μM dilutions of test compound are prepared using buffer from a 10 mM solution of test compound in DMSO. 100 μM cyclothiazide solution is prepared is by adding 3 μl of 100 mM cyclothiazide to 3 mL of buffer. Control buffer solution is prepared by adding 1.5 μl DMSO to 498.5 μl of buffer.

Each test is then performed as follows. 200 μl of control buffer in each well is discarded and replaced with 45 μl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 μl of buffer and 45 μl of test compound in buffer in appropriate wells. A second fluorescent reading is taken after 5 minutes incubation. 15 μl of 400 μM glutamate solution is then added to each well (final glutamate concentration 100 μM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 μM cyclothiazide.

In another test, HEK293 cells stably expressing human GluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylenenitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

| | Quantity (mg/capsule) |
|---|---|
| Active Ingredient | 250 |
| Starch, dried | 200 |
| Magnesium Stearate | 10 |
| Total | 460 |

The above ingredients are mixed and filled into hard gelatin capsules in 460 mg quantities.

Formulation 2
Tablets each containing 60 mg of active ingredient are made as follows:

| | Quantity (mg/tablet) |
|---|---|
| Active Ingredient | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

As used herein the term "active ingredient" refers to a compound of formula I. The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein, the terms "treating" or "to treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of formula I can be administered by a variety of routes including oral, rectal, transdermal, subcutaneous, intravenous, intramuscular, bucal or intranasal routes. Alternatively, the compounds of formula I may be administered by continuous infusion. A typical daily dose will contain from about 0.01 mg/kg to about 100 mg/kg of the compound of formula I. Preferably, daily doses will be about 0.05 mg/kg to about 50 mg/kg, more preferably from about 0.1 mg/kg to about 25 mg/kg.

We claim:

1. A compound of the formula:

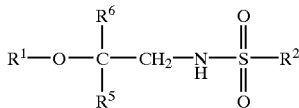

wherein
$R^1$ represents an unsubstituted or substituted aromatic group, or an unsubstituted or substituted heteroaromatic group;
$R^2$ represents isopropyl;
$R^5$ represents hydrogen; and
$R^6$ represents (1–6C)alkyl;
or a pharmaceautically acceptable salt thereof but excluding the compound [(methylethyl)sulfonyl]{2-[4-(3-(2-thienyl)phenyl)phenoxy]propyl}amine.

2. A compound according to claim 1 wherein $R^6$ represents methyl.

3. A compound according to claim 2 wherein $R^1$ represents an unsubstituted or substituted aromatic group.

4. A compound according to claim 2 wherein $R^1$ represents a naphthyl group or a phenyl, furyl, thienyl or pyridyl group which is unsubstituted or substituted by one or two substitutes selected independently from halogen; nitro; cyano; hydroxymino; (1–10C)alkyl; (2–10C)alkenyl; (2–10C)alkynyl; (3–8C) cycloalkyl; hydroxy(3–8C)cycloalkyl; oxo(3–8C)cycloalkyl; halo(1–10C)alkyl; $(CH_2)_y$ $X^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidnyl, pyrrodinyl, piperdinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropryanyl; dihydrothiazolyl; (1–4C) alkoxycarbonyldiydrothlazolyl; (1–4) alkoxycarbonyldimethyldihydro-thiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$-$(L^a)_n$-$X^2$-$(L^b)_m$ in which $X^2$ represents a bond O, NH, S, SO, $SO_2$, CO, CH(OH), CONH, NHCO, NHCONH, NHCOO, COCONH, $OCH_2CONH$ or CH=CH, $L^a$ and $L^b$ each represents(1–4C) alkalyne, one of n and m is 0 or 1 and the other is 0, and $R^{14}$ represents a phenyl or heteroaromatic group which is unsubstituted or substituted by one or two of halogen, nitro, cyano, hydroxyimino, (1–10C)alkyl, (2–10C)alkenyl, (2–10C) alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which x is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NH^{17}$, NHCONH, $OCONR^{19}$, N(CO(1–4C)alkyl)CO, or $NR^{19}COO$, $R^{15}$ represents hydrogen, (1–10C)alkyl, phenyl (1–4C)alkyl, halo(1–10C)alkyl, (1–4C)alkoxycarbonyl (1–4C)alkyl, (1–4C)alkylsulfonylamino(1–4C)alkyl, (1–4C)alkylaminosulfonyl(1–4C)alkyl, (N-(1–4C) alkoxycarbonyl)(1–4C)alkylsulfonylamino-(1–4C)alkyl, (3–10C)alkenyl, (3–10C)alkynyl, (3–8C)-cyctoalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azelidinyl, pyrrolidinyl, piperidinyl or morpholino group.

5. A compound according to claim 3 wherein $R^1$ represents an unsubstituted or substituted phenyl.

6. A compound according to claim 5 wherein the phenyl is substituted by halogen; nitro; cyano; (1–10C)alkyl; (2–10C)alkenyl; (2–10C)alkynyl; (3–8C)cycloalkyl; halo (1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR_{12}CO$, $NR_{12}COCOO$ or $OCONR^{13}$, $R^9$ represents hydrogen, (1–10C)alkyl, (3–10C)alkenyl, (3–10C) alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl (1–4C)alkylpiperazlnyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydro-thiazolyl; tetrahydrothienyl; tetrahydrofuryl; tetrahydrothiopyranyl; tetrahydropyranyl; indolyl; benzofuryl; benzothlenyl; benzimidazolyl; and a group of formula $R^{14}$-$(L^a)_n$-$X^2$-$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C) alkylene, one of n and m is 0 or 1 and the other is 0, and $R^{14}$ represents a phenyl or heteroaromatic group which is unsubstituted or substituted by one or two of halogen, nitro, cyano, hydroxylmino, (1–10C) alkyl, (2–10C)alkenyl, (2–10C) alkynyl, (3–8C)-cycloalkyl, 4-(1,1-dioxotetrahydro-1,2-thiaezinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, NHCONH, $OCONR^{19}$, N(CO(1–4C)alkyl)CO, or $NR^{19}COO$, $R^{15}$ represents hydrogen, (1–10C)alkyl, phenyl (1–4C)alkyl, halo(1–10C)alkyl, (1–4C)alkoxycarbonyl (1–4C)alkyl, (1–4C)alkylsulfonylamino(1–4C)alkyl, (1–4C)alkylaminosutfonyl(1–4C)alkyl, (N-(1–4C) alkoxycarbonyl)(1–4C)atkylsulfonylamino-(1–4C)alkyl, (3–10C)alkenyl, (3–10C)alkynyl, (3–8C)-cycloalkyl, camphoryl or an aromatic or heleroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

7. A compound according to claim 6 wherein the phenyl is substituted by a group of formula $R^{14}$-$(L^a)_n$-$X^2$-$(L^b)_m$ wherein n and m are both 0, and $X^2$ is a bond.

8. A compound according to claim 7 wherein $R^{14}$ represents a phenyl which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, NHCONH, $OCONR^{19}$, N(CO (1–4C)alkyl)CO, or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C) alkylsulfonylamino(1–4C)alkyl, (1–4C)alkylaminosulfonyl (1–4C)alkyl, (N-(1–4C)alkoxycarbonyl)(1–4C) alkylsulfonylamino-(1–4C)alkyl, (3–10C)alkenyl, (3–10C) alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

9. A compound according to claim 8 wherein $R^{14}$ represents a phenyl which is substituted by one or two of halogen, nitro, cyano, (1–10C) alkyl, (2–10C)alkenyl, halo(1–10C) alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CNR^{17}$, $NR^{18}CO$, $NHSO_2$, $SO_2NH$, $NHSO_2NR^{17}$, NHCONH, $OCONR^{19}$, N(CO(1–4C)alkyl)CO, or $NR^{19}COO$, $R^{15}$ represents hydrogen, (1–10C)alkyl, phenyl(1–4C)alkyl, halo(1–10C) alkyl, (1–4C)alkoxycarbonyl(1–4C)alkyl, (1–4C) alkylsulfonylamino(1–4C)alkyl, (1–4C)alkylaminosulfonyl (1–4C)alkyl, (N-(1–4C)alkoxycarbonyl)(1–4C) alkylsulfonylamino-(1–4C)alkyl, (3–10C)alkenyl, (3–10C) alkynyl; (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C) alkyl, or $R^{16}$ and $R^{16}$, $R^{17}$, $R^{18}$ or $R^{19}$ together with the nitrogen atom to which they are attached form an azetidinyl, pyrrolidinyl, piperidinyl or morpholino group.

10. A compound according claim 9 wherein $R^{14}$ represents a phenyl which is substituted by one or two of halogen, nitro, cyano, (1–10C) alkyl, halo(1–10C)alkyl, cyano (2–10C)alkenyl, phenyl, and $(CH_2)_zX^3R^{15}$ in which z is 0 or an integer of from 1 to 4, $X^3$ represents O, S, $NR^{16}$, COO, $CONR^{17}$, $NR^{18}CO$, $NHSO_2$, $SO_2NH$, $OCONR^{19}$, N(CO (1–4C)alkyl)CO, or $NR^{19}COO$, $R^{15}$ represents hydrogen, (1–10C)alkyl, phenyl(1–4C)alkyl, halo(1–10C)alkyl, (3–10C)alkenyl, (3–8C)-cycloalkyl, (1–4C) alkylaminosulfonyl(1–4C)alkyl, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form a pyrrolidinyl, piperdinyl or morpholino group.

11. A compound selected from the group consisting of:
[2-(4-bromophenoxy)propyl][(methylethyl)sulfonyl]amine;
[(methylethyl)sulfonyl]{2-[4-(3-thienyl)phenyl)phenoxy]propyl}amine;
{2-[4-(3-aminophenyl)phenoxy]propyl}[(methylethyl)sulfonyl]amine;
[(methylethyl)sulfonyl][2-(4-phenylphenoxy)propyl]amine;
2-[4-(2-chlorophenyl)phenoxy]propyl)[(methylethyl)sulfonyl]amine;
[(methylethyl)sulfonyl]{2-[4-(3-methylphenyl)phenoxy]propyl)}amine;
{2-[4-(4-chlorophenyl)phenoxy]propyl}[(methylethyl)sulfonyl]amine;
{2-[4-(3-chlorophenyl)phenoxy]propyl}[(methylethyl)sulfonyl]amine;
[(methylethyl yl)phenoxy)propyl][(methylethyl)sulfonyl]amine;
[(methylethyl)sulfonyl]{2-[4-(4-methylphenyl)phenoxy]propyl}amine;
3-[4-(1-methyl-2-{[(methylethyl)sulfonyl]amino}ethoxy)phenyl]benzaldehyde;
[(methylethyl)sulfonyl](2-{4-[3-(trifluoromethyl)phenyl]phenoxy}propyl)amine;
2-[4-(1-methyl-2-{[(methylethyl)sulfonyl]amino}ethoxy)phenyl]benzaldehyde;
[(methylethyl)sulfonyl](2-{4-[4-(trifluoromethyl)phenyl]phenoxy}propyl)amine:
{2-[4-(4-methoxyphenyl)phenoxy]propyl}[(methylethyl)sulfonyl]amine;
{2-[4-(2-fluorophenyl)phenoxy]propyl}[(methylethyl)sulfonyl]amine;
{2-[4-(4-fluorophenyl)phenoxy]propyl}[(methylethyl)sulfonyl]amine;
{2-[4-(3-methoxyphenyl)phenoxy]propyl}[(methylethyl)sulfonyl]amine;
{2-[4-(3-fluorophenyl)phenoxy]propyl}[(methylethyl)sulfonyl]amine;)sulfonyl]{2-[4-(2-methylphenyl)phenoxyl]propyl}amine;
[(methylethyl)sulfonyl]{2-[4-(4-(2-thienyl)phenyl)phenoxy]propyl}amine;
4-[4-(1-methyl-2-{[(methylethyl)sulfonyl]amino}ethoxy)phenyl]benzaldehyde;
[2-4-(2H-benzo[3,4-d]1,3-dioxolan-5-[(methylethyl)sulfonyl](2-{4-[2-(trifluoromethyl)phenyl]phenoxy}propyl)amine;
{2-[4-(4-cyanophenyl)phenoxy]propyl}[(methylethyl)sulfonyl]amine;
2-{4-[4-(1-methyl-2-{[(methylethyl)sulfonyl]amino}ethoxy)phenyl]phenyl}ethanenitrile;
[(methylethyl)sulfonyl][2-(4-{3-[(methylsulfonyl)amino]phenyl}phenoxy)propyl]amine;
ethyl 4-[4-(1-methyl-2-{[(methylethyl)sulfonyl]amino}ethoxy)phenyl]benzoate;
N-{4-[4-(1-methyl-2-{[(methylethyl)sulfonyl]amino}ethoxy)phenyl]phenyl}acetamide;
2-methyl-N-{4-[4-(1-methyl-2-{[(methylethyl)sulfonyl]amino}ethoxy)phenyl]phenyl}propanamide;
[(methylethyl)sulfonyl]{2-[4-(3-{[(methylethyl)sulfonyl]amino}phenyl)phenoxy]propyl}amine;
(2-{4-[4-(aminomethyl)phenyl]phenoxy}propyl)[(methylethyl)sulfonyl]amine hydrochloride;
[(methylethyl)sulfonyl]({4-[4-(1-methyl-2-{[(methylethyl)sulfonyl]amino}ethoxy)phenyl]phenyl}methyl)amine;
{(methylethyl)sulfonyl](2-{4-[4-({[(trifluoromethyl)sulfonyl]amino}methyl)phenyl]phenoxy}propylamine;
2-methyl-N-({4-[4-(1-methyl-2-{[(methylethyl)sulfonyl]amino}ethoxy)phenyl]phenyl}methyl)propanamide;
{[(methylethyl)sulfonyl]{2-[4-(4-{[(methylsulfonyl)amino]methyl}phenyl)phenoxy]propyl}amine;
N-({4-[4-(1-Methyl-2-{[(methylethyl)sulfonyl]amino}ethoxy)phenyl]phenyl}methyl)acetamide;
(tert-butoxy)-N-(2-{4-[4-(1-methyl-2-{[(methylethyl)sulfonyl]amino}ethoxy)phenyl]phenyl}ethyl)carboxamide;
(2-{4-[4-(2-aminoethyl)phenyl]phenoxy}propyl)[(methylethyl)sulfonyl]amine hydrochloride;
[(methylethyl)sulfonyl](2-{4-[4-(2-{[(methylethyl)sulfonyl]amino}ethyl)phenyl]phenoxy}propyl)amine;
N-(2-{4-[4-(1-methyl-2-{[(methylethyl)sulfonyl]amino}ethoxy)phenyl]phenyl}ethyl)acetamide;
2-methyl-N-(2-{4-[4-(1-methyl-2-{[(methylethyl)sulfonyl]amino}ethoxy)phenyl]phenyl}ethyl)propanamide;
[(methylethyl)sulfonyl]{2-[4-(4-{2-[(methylsulfonyl)amino]ethyl}phenyl}phenoxy)propyl}amine;
[(methylethyl)sulfonyl](2-{4-[4-(2-{[(trifluoromethyl)sulfonyl]amino}ethyl)phenyl]phenoxy}propyl)amine;
4-[4-((1R)-1-methyl-2-{[(methylethyl )sulfonyl]amino}ethoxy)phenyl]benzenecarbonitrile;
[(methylethyl)sulfonyl](2-{4-[4-(1-methyl-2-{[(methylethyl)sulfonyl]amino}ethoxy)phenyl]phenoxy}propyl)amine;
N-acetyl-N-{3-[4-(1-methyl-2-{[(methylethyl)sulfonyl]amino}ethoxy)phenyl]phenyl}acetamide;
methyl 4-[4-(1-methyl-2-{[(methylethyl)sulfonyl]amino}ethoxy)phenyl]benzoate;
4-[4-(1-methyl-2-{[(methylethyl)sulfonyl]amino}ethoxy)phenyl]benzoic acid;
[(2S)-2-(4-{3-[(methylsulfonyl)amino)phenyl}phenoxy}propyl][(methylethyl)sulfonyl]amine;
[(2R)-2-(4-{3-[(methylsulfonyl)amino]phenyl}phenoxy)propyl][(methylethyl)sulfonyl]amine; and
4-[4-((1S)-1-methyl-2-{[(methylethyl)sulfonyl]amino}ethoxy)phenyl]benzenecarbonitrile;
or a pharmaceutically acceptable salt thereof.

12. A pharmaceutical composltion, which comprises a compound according to claim 1 and a pharmaceutically acceptable diluent or carrier.

13. A method of potentiating glutamate receptor function in a patient, which comprises administering to said patient an effective amount of a compound of formula:

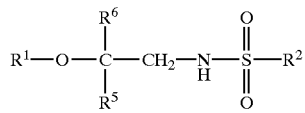

wherein
$R^1$ represents an unsubstituted or substituted aromatic group, or an unsubstituted or substituted heteroaromatic group;
$R^2$ represents isopropyl;

$R^5$ represents hydrogen; and $R^6$ represents (1–6C)alkyl;

or a pharmaceutically acceptable salt thereof but excluding the compound [(methylethyl)sulfonyl]{2-[4-(3-(2-thienyl)phenyl)phenoxy]propyl}amine.

14. A method of treating depression in a patient, which comprises administering to said patient an effective amount of a compound of formula:

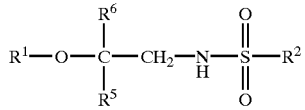

wherein $R^1$ represents an unsubstituted or substituted aromatic group, or an unsubstituted or substituted heteroaromatic group;

$R^2$ represents isopropyl;

$R^5$ represents hydrogen; and $R^6$ represents (1–6C)alkyl;

or a pharmaceutically acceptable salt thereof but excluding the compound [(methylethyl)sulfonyl]{2-[4-(3-(2-thienyl)phenyl)phenoxy]propyl}amine.

15. A method for improving memory or learning ability in a patient, which comprises administering to said patient an effective amount of a compound of formula:

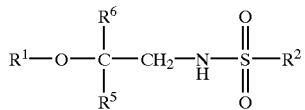

wherein $R^1$ represents an unsubstituted or substituted aromatic group, or an unsubstituted or substituted heteroaromatic group;

$R^2$ represents isopropyl;

$R^5$ represents hydrogen; and $R^6$ represents (1–6C)alkyl;

or a pharmaceutically acceptable salt thereof but excluding the compound [(methylethyl)sulfonyl]{2-[4-(3-(2-thienyl)phenyl)phenoxy]propyl}amine.

16. A method of treating Alzheimer's Disease in a patient, which comprises administering to said patient an effective amount of a compound of formula:

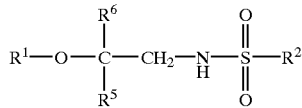

wherein $R^1$ represents an unsubstituted or substituted aromatic group, or an unsubstituted or substituted heteroaromatic group;

$R^2$ represents isopropyl;

$R^5$ represents hydrogen; and $R^6$ represents (1–6C)alkyl;

or a pharmaceutically acceptable salt thereof but excluding the compound [(methylethyl)sulfonyl]{2-[4-(3-(2-thienyl)phenyl)phenoxyl]propyl}amine.

17. A method of treating psychosis or cognitive deficits associated with psychosis in a patient, which comprises administering to said patient an effective amount of a compound of formula:

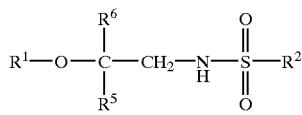

wherein $R^1$ represents an unsubstituted or substituted aromatic group, or an unsubstituted or substituted heteroaromatic group;

$R^2$ represents isopropyl;

$R^5$ represents hydrogen; and $R^6$ represents (1–6C)alkyl;

or a pharmaceutically acceptable salt thereof but excluding the compound [(methylethyl)sulfonyl]{2-[4-(3-(2-thienyl)phenyl)phenoxy]propyl}amine.

* * * * *